US012749585B2

(12) United States Patent
Aman et al.

(10) Patent No.: US 12,749,585 B2
(45) Date of Patent: Sep. 29, 2026

(54) MEASUREMENT AUTHENTICATING WELLNESS DEVICES

(71) Applicants: James Aman, Celebration, FL (US); Jeffrey Cheesman, Hamburg, NJ (US)

(72) Inventors: James Aman, Celebration, FL (US); Jeffrey Cheesman, Hamburg, NJ (US)

( * ) Notice: Subject to any disclaimer, the term of this patent is extended or adjusted under 35 U.S.C. 154(b) by 185 days.

(21) Appl. No.: 18/698,224

(22) PCT Filed: Oct. 23, 2022

(86) PCT No.: PCT/US2022/047511
§ 371 (c)(1),
(2) Date: Apr. 3, 2024

(87) PCT Pub. No.: WO2023/076130
PCT Pub. Date: May 4, 2023

(65) Prior Publication Data

US 2024/0412874 A1 Dec. 12, 2024

Related U.S. Application Data

(60) Provisional application No. 63/271,360, filed on Oct. 25, 2021.

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/0205* (2013.01); *A61B 5/117* (2013.01); *A61B 5/1171* (2016.02);
(Continued)

(58) Field of Classification Search
CPC ... A61B 5/6823; A61B 5/6826; A61B 5/6838; A61B 5/6831; A61B 5/6844;
(Continued)

(56) References Cited

U.S. PATENT DOCUMENTS 10,601,818 B2 * 3/2020 Le Saint ................. H04L 63/08
2011/0275940 A1 * 11/2011 Nims ..................... A61B 5/222 600/483
(Continued)

FOREIGN PATENT DOCUMENTS

WO WO-2018070084 A1 * 4/2018 ........... A61B 5/1172

*Primary Examiner* — Tan Doan

(57) ABSTRACT

A wearable device for allowing a person to privately self-authenticate that data determined or collected by the device is "of the person." Applications include a wellness device for determining measurements of the person's health, where then the measurements are assured to be of the person. The preferred configuration is a traditional "smartwatch" or "fitness tracker" that Includes traditional sensors for determining biometric Information from the wrist including a wrist pulse. The wearable comprises a fingerprint reader that also determines the finger pulse substantially simultaneously with reading the fingerprint. Self-authentication is accomplished by first securing the wearable to the person, second and substantially simultaneously determining the fingerprint, finger pulse, and wrist pulse, and third if the finger and wrist pulse are determined to be substantially matching, then the fingerprint is accepted as identification of the person and serves as an ID for aggregating person data up until the point the wearable is determined to be unsecured.

20 Claims, 8 Drawing Sheets

(51) Int. Cl.

| | |
|---|---|
| ***A61B 5/0205*** | (2006.01) |
| ***A61B 5/117*** | (2016.01) |
| ***A61B 5/1171*** | (2016.01) |
| ***A61B 5/1172*** | (2016.01) |
| ***A61B 5/282*** | (2021.01) |
| *A61B 5/024* | (2006.01) |

(52) U.S. Cl.
CPC ............ *A61B 5/1172* (2013.01); *A61B 5/282* (2021.01); *A61B 5/681* (2013.01); *A61B 5/02438* (2013.01); *A61B 5/1176* (2013.01)

(58) Field of Classification Search
CPC .. A61B 5/7275; A61B 5/742; G06V 40/1365; G06V 40/70; G06V 40/15; A44C 5/0007; G06F 21/32
See application file for complete search history.

(56) References Cited

U.S. PATENT DOCUMENTS

2017/0011210 A1* 1/2017 Cheong .................. A61B 5/681
2018/0026973 A1* 1/2018 Le Saint ............... H04W 12/06

* cited by examiner

2 Secondary Device(s)

3 Tertiary Device(s)

Fig. 4D
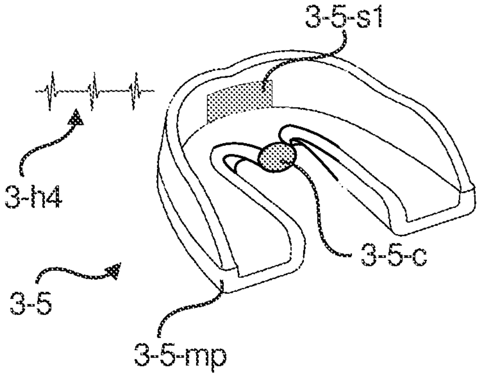
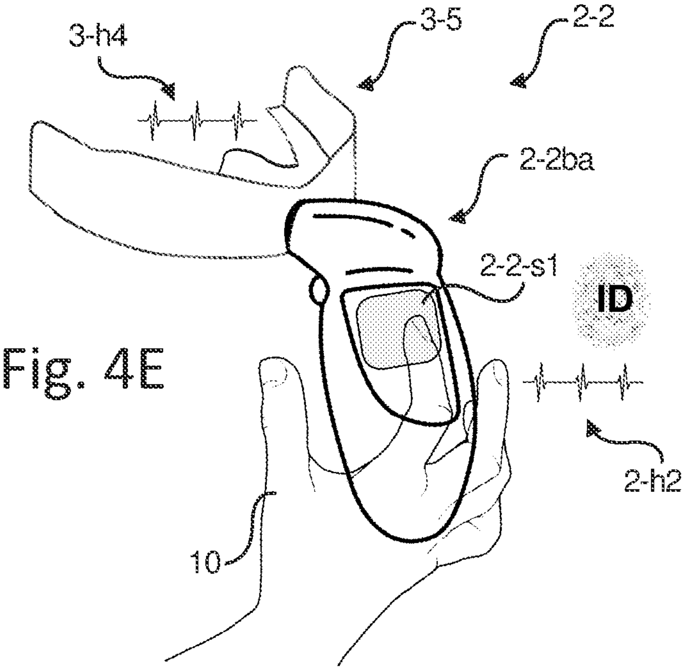
Fig. 4E

MEASUREMENT AUTHENTICATING WELLNESS DEVICES

CROSS-REFERENCE TO RELATED APPLICATIONS

The present provisional application is a continuation-in-part of the PCT Non-Provisional Application No. PCT/US2021/029186 entitled GUEST TRACKING AND ACCESS CONTROL USING HEALTH METRICS filed on Apr. 26, 2021. This application claims the benefit of U.S. Provisional Application No. 63/271,360 entitled MEASUREMENT AUTHENTICATING WELLNESS DEVICES filed on Oct. 25, 2021.

FIELD OF INVENTION

The present invention relates to an entity access control system that allows or denies access by a person to a premises or gathering based upon the anonymous confirmation of an authenticated health state provided by a computing device associated of the person attempting to gain access. The health state is determined by an intermediary app executing on the computing device, where the device authenticates one or more health measurements for determining the authenticated health state, and where the one or more authenticated health measurements are determined by the computing device or in combination with an authenticated companion device.

BACKGROUND OF THE INVENTION

The present invention is related to THEME PARK GAMIFICATION, GUEST TRACKING AND ACCESS CONTROL SYSTEM, Aman, U.S. Pat. No. 10,861,267, issued Dec. 8, 2020. The GUEST TRACKING AND ACCESS CONTROL SYSTEM taught a "smart ticket" comprising in one form a mobile device such as a smartphone executing a venue app. Using the smart ticket in combination with a venue's "confined Zone3" (herein also "geofence") it was taught that that a ticketed guest could negotiate "confirmed" self-access to the venue, where confirmation included self-identification using a current biometric to compare with a prior biometric for example already "registered" to the ticket (herein referred to as "authentication"). The venue app was a tamperproof agent representing both parties, the guest, and the venue ("destination"). The solution maintains guest privacy and eliminates the need for a personal interaction with a destination agent, while also achieving the trust of the destination (i.e., that the ticket is only being used by a single biometrically confirmed/authenticated person). This prior teaching is generally referred to herein as a premises access control system implementing an anonymous, privately authenticated "right-to-access" using an "honest broker" (the venue app).

The present invention is also a continuation-in-part of GUEST TRACKING AND ACCESS CONTROL USING HEALTH METRICS, Aman et al., PCT/US2021/029186 filed on Apr. 26, 2021. This subsequent PCT application extended the prior U.S. Pat. No. 10,861,267 teachings to include means for assuring the destination of the acceptable present health state of the guest, referred to as "proof-of-health." Within this PCT patent the prior "venue app" is also referred to as an "intermediary app" or "honest broker." The honest broker app is shown to gain the "public trust" that a person desiring to access a premises or gathering has an acceptable health status, where this acceptable proof-of-health is privately determined and authenticated by the honest broker with respect to one or more public "regiments" specifying the conditions for proof.

Proof-of-health was shown to have at least three dimensions including: "level 1" (L1) personal symptom tracking, level 2 (L2) health kit test result(s), and level 3 (L3) healthcare administered services (such as vaccination(s)). All data supporting L1, L2 and L3 proof was shown to be collected and maintained by the honest broker remaining private to the person where only the net "regiment pass/fail" status is shared with the access control system. Thus, the system was shown to implement an anonymous, privately authenticated "right-to-access" with "proof-of-health" using the "honest broker."

L1 symptom tracking was shown to require further adapted wellness devices (examples included a digital thermometer, pulse oximeter, a smartwatch, chest band, smart scale, patch, breath analyzer, etc.). While traditional wellness devices can be used in private by a person to collect health measurements indicative of their personal symptomatic (L1) health state, it was shown that these traditional measurements where not authenticated to be "of" the person, and therefore were not "publicly trustable." Gaining public trust was shown to require authentication of each measurement by at least either of two methods referred to generally as "line-of-sight" and "non-line-of-sight."

In line-of-sight authentication, the person holds their computing device with camera (e.g., smartphone) where the honest broker app (executing on or through the computing device) can simultaneously image the person's face along with the wellness device. While simultaneously viewing, the app: 1) confirms the person's identity using facial recognition, 2) sends electronic signals to the device for triggering a unique pattern of light flashes, where the device is adapted with an LED (or includes a light emitter) to blink a return signal, and 3) detects and confirms the return signal while the device simultaneously measures and communicates the person's symptom(s).

When line-of-sight is not possible, e.g., the person is wearing a chest band or an arm patch, the app: 1) confirms the person's identity using facial recognition, 2) using remote Photoplethysomography (rPPG) detects the person's heartbeat (H1), while the wellness device separately detects the person's heartbeat (H2), and 3) confirms that H1 sufficiently matches H2 while the device measures and communicates the person's symptom(s).

The PCT application taught means for determining that a wearable (such as a smartwatch or chest band) was affixed and clasped to the person's body, where authentication by either method was not substantiated until the wearable was determined to be "locked" and whereafter all measurements taken (presumably over minutes, hours and even days) remain "authenticated" until the wearable detects that it has been "unlocked" from the person's body.

The preceding background is not meant to completely teach or in any way limit the prior related and continued patents and the reader is directed to these patents and patents pending for a full understanding of their many teachings and various implementations of both apparatus and methods. For example, the PCT application taught extensively about anonymous, authenticated health kits allowing a person to privately collect and authenticate health samples (such as mucus or blood) for lab analysis, where the test results (L2) are associated with an anonymous token for retrieval by the honest broker from the lab's anonymous database. The PCT application also taught extensively about anonymous, authenticated health services (such as vaccinations) where the person uses the honest broker to privately authenticate and request a particular service. The honest broker was described as providing an anonymous service token to a healthcare service agent, whereafter a healthcare service is provided to the person and whereupon completion of the service a certificate is provided to the honest broker in association with the anonymous token, thus providing "proof-of-service" (L3).

SUMMARY OF THE INVENTION

The present invention especially extends the teachings of the PCT Application GUEST TRACKING AND ACCESS CONTROL USING HEALTH METRICS, Aman et al., PCT/US2021/029186 filed on Apr. 26, 2021, of which it is a continuation-in-part. Even more specifically, the present invention deals with additional teachings relating to the authentication of wellness devices, where additional novel authentication addresses teachings related to both apparatus and methods.

Teachings are provided that generally segregate wellness devices as being "primary," "secondary," or "tertiary." Primary devices are differentiated by their ability to execute the honest broker app for determining, authenticating, maintaining, and communicating the on-going health state of a person. As taught in the related PCT application, the honest broker app authenticates and assesses the person's current health state in relation to one or more public regiments specifying rules and conditions for example referring to L1 "symptom tracking," L2 "health kit testing," and L3 "health services" (such as vaccinations), where for example the authenticated "regiment ABC pass/fail assessment" is anonymously communicated to an access control system within a geofence, and where the access control system allows or denies the person access to a premises or gathering based at least in part on the authenticated assessment/"proof-of-health."

Primary and secondary devices are differentiated herein by their ability to determine at least one personally identifying biometric of the person, such as facial recognition, voice recognition, fingerprint, iris scans or heartbeat "ECG"/"EKG" pattern, where these personally identifying biometrics are referred to as "body ID patterns (a)." Hence, primary and secondary devices are said to be "self-authenticating." A primary device is also shown to have the ability to pair and authenticate a companion device, for example a secondary or tertiary device, where the companion device is determining and providing one or more health measurement of the person to the primary device from use in determining the person's on-going heath state. In the case of pairing, both the primary device and the companion device determine a "comparison body pattern (b)" (such as the person's heartbeat), where then the primary device authenticates the companion device by comparing the pattern "b" captured by the companion device with the pattern "b" captured by the primary device.

Specific adaptations are provided for a smartwatch that include the use of a combined fingerprint reader/heartbeat detector. The adaptation is shown on the watch band and allows the watch to self-authenticate by in part comparing a simultaneous heartbeat captured from the finger (along with the fingerprint ID) with the heartbeat captured from the wrist underneath the watch itself. The self-authenticating smartwatch is shown as a primary device that is then capable of pairing with another primary device (such as a smartphone), a secondary device (such as an authenticating chest band) and a tertiary device (such as clothing with body sensors, body patches, smart scales and exercise equipment).

A method is discussed for establishing the authenticity of a person using a primary device, where the primary device is either a wearable or not a wearable, followed by the pairing, authenticating and health measurement data collection of the authenticated primary device with any of secondary or tertiary devices (where an otherwise primary device can also act as a secondary or tertiary device).

The authenticating smartwatch is also shown to include further adaptions taught in the PCT application in relation to a finger worn device, where the adaptations include skin temperature as well as galvanic response sensors, ambient sensors (for example to sense humidity, temperature and light), and an LED or otherwise light emitter for use in line-of-sight light signaling. The adaptations allow the smartwatch for example to function similar to the prior finger worn device for example to touch the person's forehead for measuring their temperature in combination with the electrical state of their skin and the surrounding ambient environmental conditions.

A new type of wellness device is taught that captures a person's heartbeat preferably from the upper lip by for example using either of transmissive or reflective photoplethysmography ("PPG"). This device is taught to couple with for example either of a breath analyzer or a digital thermometer, where the coupled combinations from at least tertiary devices, but possibly also secondary devices by the inclusion of a fingerprint/pulse detector.

Given the teachings of the prior referenced applications along with the state-of-the art in device electronics, health sensors, environment sensors, computer and communication systems and other arts as will be recognized within the present specification, it is now possible to implement primary, secondary and tertiary wellness devices as described herein and in alternative embodiments anticipated herein, all as will be apparent from a careful consideration of the present application.

BRIEF DESCRIPTION OF THE SEVERAL VIEWS OF THE DRAWING

FIG. 4D is a perspective view of lip pulse detector 3-5 comprising mouthpiece 3-5-*mp* that includes a PPG lip sensor 3-5-*s*1 and a coupling/cavity 3-5-*h* with which health measurement apparatus can be engaged by detector 3-5 for example by insertion through a cavity (see for example breath analyzer 2-2 in FIG. 4E and digital thermometer 2-3 in FIG. 5B). Mouthpiece 3-5-*mp* can take virtually any of many possible forms for engaging with the mouth of person 10 while positioning with respect to either the upper lip (as depicted in FIG. 4D) or with respect to the lower lip or even both lips (depictions not provided). Coupler/cavity 3-5-*c* preferably includes electrical contacts or communication means (not depicted) for at least detecting the presence of an inserted health measurement devices (such as 2-2 or 2-3) and optionally communicating with the inserted device. Also not depicted are any well-known wellness device elements such as power and computing components for at least operating the PPG lip sensor 3-5-*s*1, detecting the presence of an inserted measurement device and communicating with either the inserted measurement devices and/or a primary wellness device 1 such as smartphone and app 1-1 or smartwatches 1-2, 1-3. Lip sensor 3-5-*s*1 determines a lip-heartbeat 3-*h*4.

FIG. 4E depicts a breath analyzer 2-2*ba* that has been further adapted to physically and functionally combine with a lip pulse detector 3-5 for the purpose of concurrently determining the lip-heartbeat 3-*h*4 while also at least receiving/sampling the breath of person 10, and the optionally also analyzing the breath of person 10, such that the combination serves to create an authenticatable breath analysis, where it is understood that the analysis may be performed at a later time that is not necessarily substantially concurrent with the detection of lip-heartbeat 3-*h*4. Person 10 and measurement authentication can be accomplished in a number of ways as discussed in the prior PCT and the present application, including the further adaptation of the breath analyzer 2-2*ba* to include a combination fingerprint reader/heartbeat sensor 2-2-*s*1, where the finger-heartbeat 2-*h*2 determined by sensor 2-2-*s*1 is then comparable to lip-heartbeat 3-*h*4 such that upon proper matching, the fingerprint ID captured by sensor 2-2-*s*1 is useful for authenticating the concurrently determined breath analysis of person 10. Analyzer 2-2*ba* preferably at least includes apparatus for electronically engaging and/or otherwise communicating with lip pulse sensor 3-5 such that sensor 3-5 determines the time and duration of engagement, preferable used at least in part to trigger lip pulse measurement via the PPG sensor(s) 3-5-*s*1 (FIG. 4D) such as 10-*ppg*1 or 10-*ppg*2 (FIG. 4C). Analyzer 2-2*ba* may also comprise electronic components for communicating with any of a primary wellness device 1 such as smartphone and app 1-1 or smartwatch 1-2, 1-3. There are many possible arrangements and configurations of authenticating breath analyzer 2-2, where some combinations comprise a multi-part configuration including physically separable lip pulse detector 3-5 and breath analyzer unit 2-2*ba*, whereas other configurations (not depicted) form a single integrated device 2-2 with the necessary combination of apparatus and methods comprising 3-5 and 2-2*ba*.

DETAILED DESCRIPTION OF THE INVENTION

Figure 1A:
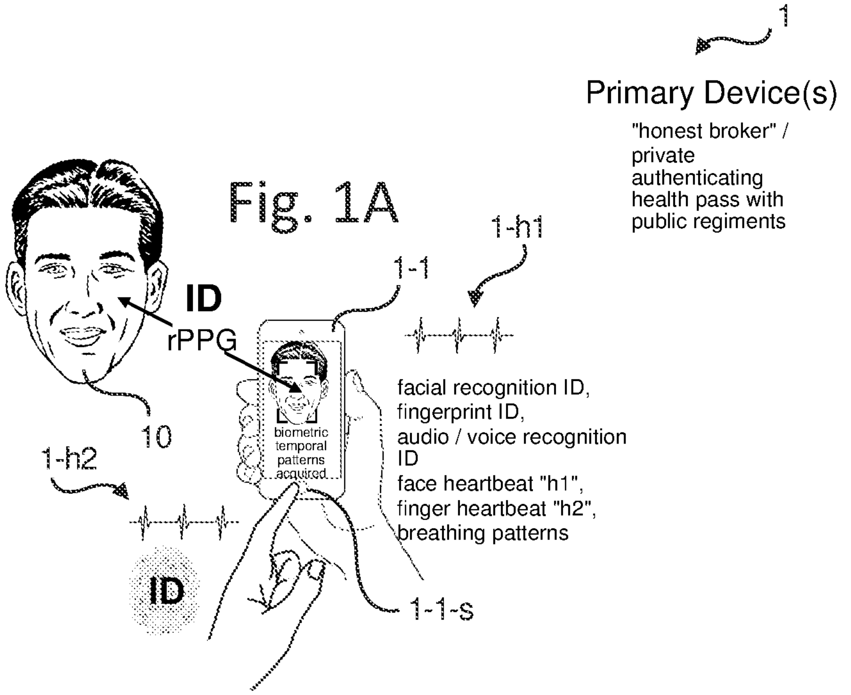
FIG. 1A shows a person 10 being authenticated by primary wellness device 1 such as a computing device with camera (e.g., the depicted smartphone) 1-1 executing an honest broker app (all as discussed in the prior related applications). Personal authentication for example includes any of facial recognition ID, fingerprint ID, and audio/voice pattern ID. Also shown is primary device 1-1 capturing a heartbeat pattern 1-*h*1 using rPPG (remote photoplethysmography), where this heartbeat is at least usable for authenticating other tertiary devices 3 that lack their own means for personal identification (ID) but otherwise can create a comparable heartbeat pattern (such as 3-*h*4 in FIGS. 1D, 1E and 1F). Device 1-1 is further adapted to include a combination fingerprint reader/heartbeat sensor 1-1-*s*, where the finger-heartbeat 1-*h*2 determined by sensor 1-1-*s* is then comparable to face-heartbeat 1-*h*1 such that upon proper matching the fingerprint ID captured by sensor 1-1-*s* is proven combinable for personal authentication with the facial ID determined via facial recognition.

Referring first to FIG. 1A, person 10 is being authenticated by primary wellness device 1 including a computing device with camera (e.g., as the depicted smartphone) 1-1 executing an honest broker app (all as discussed in the prior related applications). There is a significant body of research addressing what is often referred to as "multimodal biometric personal identification," wherein two or more forms of biometric identification are combined to increase overall accuracy. Even with a cooperating person in a constrained environment, facial recognition for example can be less than 100% accurate, exhibiting either false positives (indicating that images of two different individuals show the same person) or false negatives (the inverse problem). Worse yet, as indicated in a May 2020 NIST (National Institute of Standards and Technology) study that studies 189 software algorithms from 99 developers, "most programs exhibit different levels of accuracy depending on demographics, including sex, age, and racial background." What is preferred is that multiple forms of biometric identification are implemented on device 1-1 for substantially concurrent person 10 identification, where the multiple forms of biometric identification include but are not limited to facial, fingerprint, voice or iris scan recognition. Using at least two forms of substantially concurrent person 10 biometric identification increases the overall accuracy of identification and therefore the "public trust" of the associated honest broker 1-1 "proof-of-health" status determined regarding person 10 (see also related PCT application), where it is noted that all of the aforementioned biometric identification methods are available in current marketplace for use with at least a smartphone or mobile computing device such as preferred for primary device 1-1.

Mobile devices such as smartphones often include what is referred to as a "home button" that includes a fingerprint reader. However, over the last several years, some manufactures such as Apple have done away with the home button (and with it fingerprint detection), shifting the full burden for personal identification to facial recognition. Furthermore, in a strict sense, even traditional mobile devices that include a fingerprint reader cannot conclusively confirm that the finger being scanned is both (1) of the same person being imaged for example using facial recognition, and (2) is a "live" finger as opposed to a forged or faked fingerprint.

Companies such as Qualcomm have produced mobile fingerprint/pulse sensors additionally capable of reading the fingerprint of person 10 while also detecting the presence of blood flow and a heartbeat within the finger of person 10, helping to address the "live" finger (2) problem.

The present invention teaches the use of a mobile fingerprint/pulse sensor 1-1-*s* in a mobile device such as 1-1 preferably combined with at least concurrent, or substantially concurrent facial recognition (as depicted in FIG. 1A). Furthermore, as described in the related PCT application, during the image processing performing the facial recognition, at least using a technology referred to as "remote photoplethysmography" ("rPPG"), it is possible to detect minor color variations for example in the person 10's cheeks for use in determining the person's heartbeat 1-*h*1. (It is also important to see that traditional use of a fingerprint reader, with or without simultaneous and spatially overlapping pulse detection such as provide by the Qualcomm readers, has been limited to confirming the identity of the smartphone/device operator, and has not been applied to the authentication of health measurements as discussed herein and in the related PCT application.)

Still referring to FIG. 1A, the primary device 1-1 adapted with sensor 1-1-*s* is first capable of determining traditional biometric facial and fingerprint recognition for the separate identification of person 10, but then further capable of comparing the face heartbeat 1-*h*1 with the finger heartbeat 1-*h*2, where sufficient correlation address the "same person's face and finger" problem (1) above. Just as with hacking of the fingerprint, for example by using a rubber finger with a forged replica fingerprint, it has been shown that facial recognition systems can be hacked using printed photographs of the person 10 to be hacked. By detecting heartbeats 1-*h*2 and 1-*h*1, both forms of fingerprint and facial hacking are thwarted, and thus the concurrent combination of techniques as described herein provides even greater system integrity and therefor public trust in any determined proof-of-health related to person 10.

Mobile device with honest broker app 1-1 can use additional forms of personal identification at least including audio/voice recognition and iris scan recognition, both technologies which currently exists in mobile devices such as smartphones. When doing audio/voice recognition, it is also preferred that the person 10 being authenticated is concurrently being imaged such that the personal ID comprises: 1) confirmation via facial recognition, 2) confirmation via voice recognition, and 3) matching of lip sync tracking between the facial images and the voice patterns. When doing iris scan recognition, it is also preferred that the image processing uses rPPG to determine the person 10's pulse from the iris or from the face surrounding the eyes, where then this iris pulse can for example be compared to any of the other body pulses such as the finger pulse 1-*h*2 being concurrently captured along with the fingerprint ID.

Still referring to FIG. 1A, it is also well-known that a heartbeat can be used as a form of authentication. This heartbeat "signature" is dependent upon the peaks and valleys of the ECG (electrocardiogram) wave itself and substantially independent of the pulse rate/temporal beat pattern, where these peaks and valleys have a relationship to the structure of the heart (see the publicly available medical literature). The present invention distinguishes this type of "body ID pattern (a)" (i.e., the heartbeat signature used as an ID), from a "comparison body pattern (b)" (i.e., the heartbeat timing/temporal beat pattern used to match and correlate disparate devices/sensors), where (a) typically requires increased measurement precision as compared to (b). There are companies currently in the marketplace such as Nymi that produce wearables designed for capturing a fingerprint for an ID (a), along with a heartbeat signature for an ID (a).

What is important to see is that there are many types (modalities) of body ID patterns (a) (again, face, finger, iris, voice, heartbeat) not limited to those presently discussed or even those currently known. Using substantially concurrent measurements of multiple modalities of body ID patterns (a), a single authenticating device such as mobile device 1-1 or wearable 1-2 increases the accuracy of person 10 authentication, both minimizing "FAR" (the "false acceptance rate" where two patterns (a) of the same modality are said to be of the same person 10 but are in fact of different individuals) while also minimizing "FRR" (the "false rejection rate" where two patterns (a) of the same modality are said to be of different individuals but are in fact of the same person 10). It is also important to see that two or more different devices can each be measuring a same or different modality of body ID pattern (a) for identification (such as face and/or finger), while also picking up a like modality comparison body pattern (b) for us in correlating IDs (a) (e.g., where (b) is a temporal pattern such as an on-going heartbeat that can be compared as a temporal beat that may be insufficient for uniquely identifying the person 10 as a pattern (a), but is sufficient for concluding that the two or more different devices are determining their ID patterns (a) of the same person 10). Furthermore, it is important to see that a primary device 1 can authenticate a person 10, such as by determining one or more IDs (a), but then can also determine a comparison pattern (b) (such as a heartbeat), while additional one or more other tertiary devices 3 are only capable of determining a comparison pattern (b) (such as a heartbeat), where the authentication of person 10 by determination of (a) by the primary device 1 is then extendable to authentication of health data collected by any of the one or more additional tertiary devices 3 by sufficient correlation of the common comparison pattern (b) (e.g., the heartbeat).

Still referring to FIG. 1A, is it not necessary that fingerprint/pulse sensor 1-1-*s* be integrated as a "home button." New fingerprint readers have emerged that function underneath the screen or on the side edge of a mobile device such as 1-1. Techniques for adapting fingerprint reader technology to concurrently determine a pulse are well-know, with new technologies anticipated. What is important to see is that such a sensor 1-1-*s*, either integrated directly into mobile device 1-1, or integrated into a smartphone case (not depicted) that then secures to device 1-1 and is capable of electronic communication with device 1-1 (even drawing power from device 1-1), provides additional means useful for increasing the accuracy of authenticating person 10.

Figure 2:
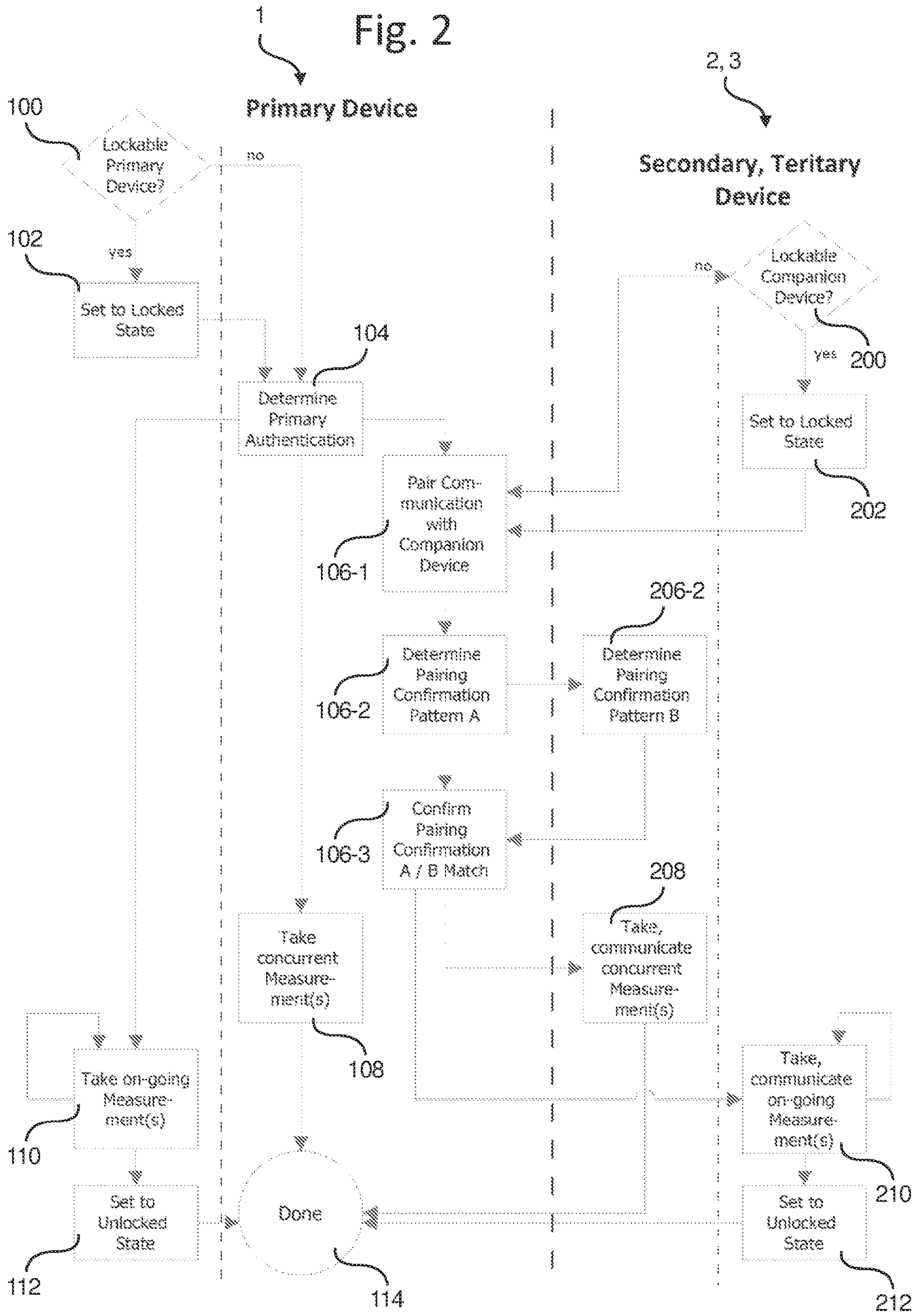
FIG. 2 is a flowchart showing the preferred steps (100 through 114) for authentication of a primary device 1, such as mobile device 1-1 or wearable/watch 1-2, followed by the collection of health measurements by the authenticated primary device 1. Steps 106-1 through 106-3 cover the pairing and authentication of a companion device 2 or 3 with the device 1 followed by the collection and communication of health measurements made by the companion device 2 or 3 (collectively steps 200 through 212). The preferred steps are not limiting, for example a secondary device 2 could follow the steps of 100 through 114 excluding device pairing steps 106-1, 106-2 and 106-3, as the conceptual distinction between a primary device 1 and a secondary device 2 is mainly that the secondary device 2 is not used to pair with other devices (such as a tertiary device 3) for the purposes of collecting additional health measurements, although many variations are possible and useful outside of this conceptual distinction.

And finally with respect to FIG. 1A, primary device 1-1 is capable of determining at least one body ID pattern (a) such as (but not limited to) a facial recognition ID, iris recognition ID, voice recognition ID or fingerprint recognition ID, as well as at least one comparison body pattern (b) such as (but not limited to) face-heartbeat 1-*h*1 or finger-heartbeat 1-*h*2, where comparison patterns (b) are useful for confirming other secondary devices 2 and tertiary devices 3, all as will be discussed further, especially in relation to upcoming FIG. 2.

Figure 1B:
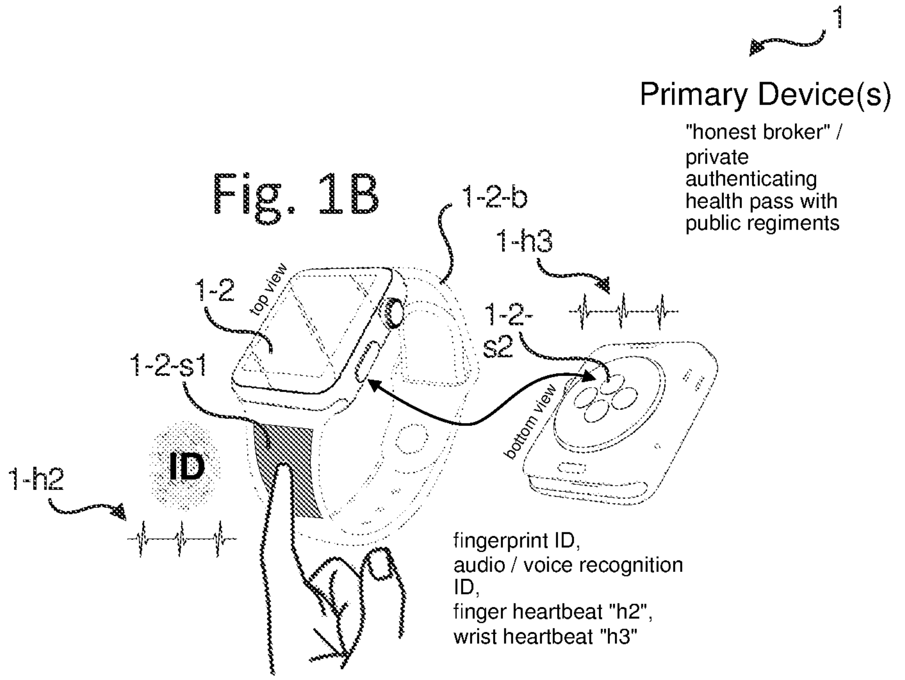
FIG. 1B shows a perspective view of a smartwatch 1-2 in both a top view (including watch band 1-2-*b*) and a bottom view showing sensor(s) 1-2-*s*2 for determining at least the wrist-heartbeat 1-*h*3 of person 10 currently wearing the watch 1-2. Watch band 1-2-*b* preferably includes any of clasp "open/closed" detection technologies such as taught in relation to the parent PCT application, (including for example the use of sensor(s) 1-2-*s*2 to sense skin/wrist proximity), where band 1-2-*b* has been further adapted to additionally include fingerprint reader/heartbeat sensor 1-2-*s*1, where the finger-heartbeat 1-*h*2 determined by sensor 1-2-*s*1 is then comparable to wrist-heartbeat 1-*h*3 such that upon proper matching the fingerprint ID captured by sensor 1-1-*s*1 is proven useable for personal authentication of the smartwatch measurements and as such the smartwatch 1-2 becomes a primary wellness device 1.

Referring next to FIG. 1B, there is shown a perspective view of a smartwatch 1-2 in both a top view (including watch band 1-2-*b*) and a bottom view showing sensor(s) 1-2-*s*2 for determining at least the wrist-heartbeat 1-*h*3 of person 10 currently wearing the watch 1-2. Typical well-known sensors for determining wrist pulse and other related information such as found in a traditional pulse-oximeter include photoplethysmography (PPG) devices (see FIG. 4C), also as discussed in the related PCT application. Many smartwatches are available in the market from brand names such as Apple, Fitbit, Garmin and Xiaomi, where smartwatches typically include a touch screen and enough processing power and communications to provide useful apps, especially in combination with a paired smartphone, such as usable for primary device 1-1. Many smartwatches also include sensors for not only determining pulse, but also other types of sensors for detecting movement and otherwise assessing exercise levels, sleep patterns or other health metrics.

The related PCT application showed how these many variations of wearables such as 1-2 (or other non-wearable primary devices such as mobile device 1-1) that determine one or more health metrics/measurements, could be further adapted to function as authenticated health tracking devices useable in combination with a private health status tracking technology. The technology and teaching of the combined related patents showed a private system for authenticating personal right-of-access (e.g., biometrically registered, and biometrically confirmed, thus authenticated ticket ownership) and/or proof-of-health (e.g., a biometrically registered on-going regiment of biometrically confirmed health measurements indicating a health status according to a public protocol, thus an authenticated health status). These authenticated right-of-access and/or proof-of-health were shown to be combinable with an access control system allowing a person to gain publicly trustable self-access to a premises or gathering without requiring pre-registry with the access control system, the sharing of personal identity, biometrics or other related data other than confirmation of compliance as tracked by the honest broker operating on the person 10's (non-wearable or wearable) primary device 1, such as 1-1 or 1-2.

Still referring to FIG. 1B, the related PCT application also taught that watch band **1-2-*b* preferably includes any of clasp "open/closed" detection technologies, (including for example the use of sensor(s) 1-2-*s*2 to sense skin/wrist proximity or electro, electro-mechanical means for determining the state of a mechanical clasp). In the present application, band 1-2-*b* has been further adapted to additionally include fingerprint (a) reader/heartbeat (b) sensor 1-2-*s*1, where the finger-heartbeat 1-*h*2 determined by sensor 1-2-*s*1, functioning as a comparison body pattern (b), is then comparable to wrist-heartbeat (b) 1-*h*3 such that upon sufficient correlation the fingerprint ID (a) captured by sensor 1-1-*s*1 is proven useable for personal authentication of the smartwatch measurements as "belonging to" or "being of" person 10 and as such the smartwatch with honest broker app 1-2 becomes a primary wellness device 1, like mobile device/smartphone and honest broker app 1-1**.

What is important to see is that wearable 1-2 can determine both ID patterns (a) and comparison patterns (b). As a careful reading of the present invention and prior related applications will show, wearable 1-2 can work both in conjunction with another primary device such as 1-1, or independently given the ability for self-authentication using at least one pattern (a) such as the fingerprint determined by sensor **1-2-*s*1. Many variations of fingerprint reader/pulse detector 1-2-*s*1 are anticipated, where companies such as Qualcomm provide at least one solution. Those familiar with wearables will understand that while incorporated into a wristband 1-2-*b*, detector 1-2-*s*1 can be electrically connected to smartwatch 1-2 for example to receive power, be activated/deactivated, and to communicate detected data including the fingerprint scan(s) and finger heartbeat 1-*h*2** and related data. Alternative power, computing and communication arrangements are possible, as will be understood by those familiar with wearable technology.

Other variations of wearable 1-2 are possible without departing from the true scope and spirit of the invention, as will be apparent from a careful consideration of the present teachings, especially in consideration of wearable 1-2's ability to "pair" and "authenticate" (see FIG. 2) with another primary device, such as a smartphone 1-1. Given this paired arrangement, a person 10 can clasp a wearable such as 1-2 to their wrist, where wearable 1-2 omits sensor **1-2-*s*1 becoming a tertiary device 3 that is unable to self-authenticate, capturing neither a current fingerprint (a) nor finger heartbeat (b) 1-*h*2 of the person 10. However, using wrist sensors 1-2-*s*2, the now-tertiary wearable 1-2 can still determine a wrist heartbeat 1-*h*3 that can be confirmed during pairing and authentication by a primary wellness device such as smartphone 1-1, where confirmation for example includes correlating the wrist heartbeat 1-*h*3 with either or both of a face heartbeat 1-*h*1 or a finger heartbeat 1-*h*2 determined by the primary device 1-1**.

In yet another possible variation of wearable 1-2, sensors **1-2-*s*2 for example can be further adapted to determine a heartbeat "ECG"/"EKG" signature of the person 10, where this heartbeat signature can serve as both a body ID pattern (a) and a confirmation body pattern (b). Current literature indicates that the heartbeat signature is accurate, but not as accurate as for example a fingerprint. None-the-less, this ECG/EKG technology may improve and otherwise the accuracy in some situations may be considered sufficient for then allowing the further adapted wearable to authenticate the person 10 using a heartbeat signature (a) captured by sensors 1-2-*s*2, rather than a fingerprint (a) captured by sensors 1-2-*s*1, (or a combination solution capturing both the heartbeat (a) and fingerprint (a) could be used to increase public trust and accuracy). Since a wearable such as a smartwatch 1-2 includes a user interface, it is also possible to accept a user password or similar, for combination with either or both the heartbeat (a) and the fingerprint (a) for personal authentication, after which heartbeat (b) can be used by the wearable 1-2 for pairing and authenticating with other companion devices (see FIG. 2**).

Figure 1C:
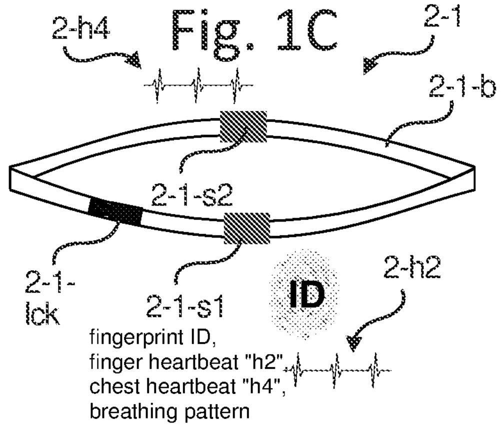
FIG. 1C shows a secondary wellness device 2 that is a wearable chest band 2-1 comprising band 2-1-*b* including "open/close" detectable lock 2-1-*lck*, a sensor 2-1-*s*1 for detecting a fingerprint with associated heartbeat 2-*h*2, and at least one sensor 2-1-*s*2 for detecting body cavity health data including heartbeat 2-*h*4. Finger-heartbeat 2-*h*2 determined by sensor 2-1-*s*1 is then comparable to body-heartbeat 2-*h*4 such that upon proper matching the fingerprint ID captured by sensor 2-1-*s*1 is proven useable for personal authentication and as such the chest band 2-1 becomes a secondary wellness device 2.

Referring next to FIG. 1C there is shown a secondary wellness device 2 that is a wearable chest band 2-1 including further adaptations of a sensor **2-1-*s*1 for detecting a fingerprint (a) with associated heartbeat (b) 2-*h*2, like the adaptations to primary wellness devices 1-1 and 1-2. As prior stated, a secondary device 2 (like a primary device 1) can self-determine one or more (ID) (a) patterns for self-authenticating any health measurements determined by the secondary device 2, whereas unlike a primary device 1 a secondary device 2 is limited for example to not include the honest broker app functions such as maintaining an on-going health state with a net "proof-of-health" status (where those familiar with device computing and associated power requirements will understand the benefits of such limitations). However, as will be clear from a careful understanding, the distinctions of primary 1, secondary 2, and tertiary 3 devices are for instructive purposes and not meant to be strictly limiting. For example, a chest band 2-1 in some variants can be further adapted to be a primary device 1 or a tertiary device 3**, and thus the present invention should not be limited by these exemplary device categorizations.

Still referring to FIG. 1C, chest band 2-1 was first described in the related PCT application that taught a chest band **2-1-*b* including "open/close" detectable lock 2-1-*lck*, and at least one sensor 2-1-*s*2 for detecting body cavity health data including heartbeat 2-*h*4. (The additional features and function of chest band 2-1, like other devices first discussed in the related PCT application, are useful and combinable with the teachings herein, even if not explicitly or implicitly referenced. For example, chest band 2-1 preferably includes power, computing and communication means for operating the one or more sensors such as 2-2-*s*1, 2-2-*s*2, 2-1-*lck*, and processing/communicating health data to presumably a primary wellness device such as 1-1 or 1-2**.)

As with the discussion of advantages and uses for including sensor 2-1-$s$1 to preferably concurrently determine an body ID pattern (a) (such as a fingerprint) while substantially simultaneously determining a confirmation body pattern (b) (such as the finger heartbeat 2-$h$4), this further adaptation of the chest band 2-1 enables the band 2-1 to function as a secondary wellness device 2 (thus authenticating its own health measurements), and not just a tertiary wellness device 3 (for capturing health measurements with concurrent or pre-authenticated body patterns (b) but without ID patterns (a), all as will be well understood by a careful reading of the present invention and the related PCT application). Thus, further adapted chest band 2-1 is useful for both identification (a) of person 10 and the capturing and authentication of at least one health measurement relating to or "of" person 10, such as but not limited to resting heart rate, breathing patterns including shortness of breath, cough patterns, sleep patterns, etc.

Figure 1D:
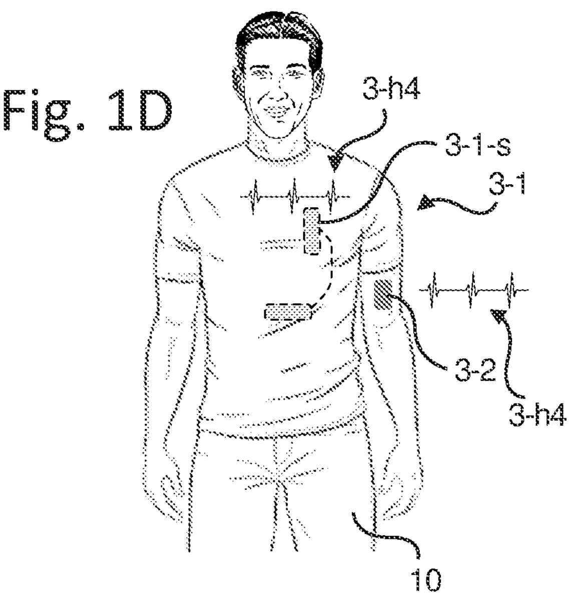
FIGS. 1D, 1E and 1F show four variations of a tertiary wellness devices 3, including wearable clothing 3-1 and wearable patch 3-2 (see FIG. 1D), smart scale 3-3 (FIG. 1E), and exercise equipment 3-4 (FIG. 1F). Each variation can detect a body heartbeat pattern 3-*h*4 for association with any determined health measurements, where the associated health measurements are then authenticatable by a primary device 1 based upon sufficient matching of pattern 3-*h*4 with a body heartbeat pattern separately and preferably concurrently determined by the device 1 (such as face-heartbeat 1-*h*1, finger-heartbeat 1-*h*2 or wrist-heartbeat 1-*h*3).
Figure 1E:
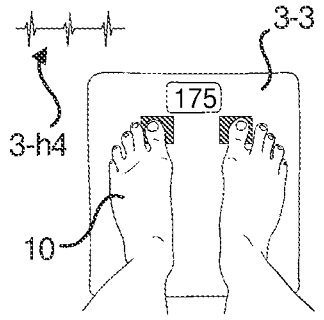
Figure 1F:
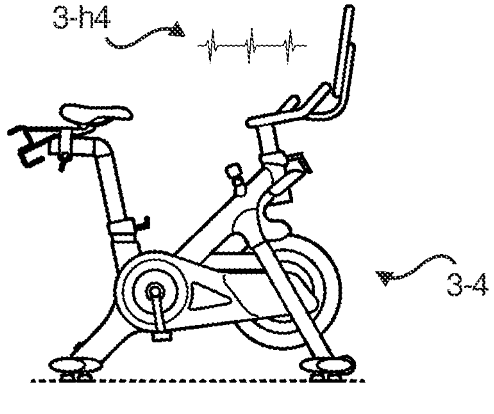

Referring next collectively to tertiary wellness devices 3 as depicted in FIGS. 1D, 1E and 1F, there is shown respectively an example of: 1) a person 10 wearing clothing 3-1 comprising sensor(s) 3-1-$s$ capable of sensing a confirmation body pattern (b) such as heartbeat 3-$h$4 along with at least one health measurement/metric, and 2) a person 10 wearing a body patch 3-2, 3) a person 10 standing on a smart scale 3-3, and 4) an exercise apparatus 3-4 for use by a person 10, where like clothing 3-1, each of body patch 3-2, smart scale 3-3 and exercise apparatus 3-4 are capable of determining person 10's heartbeat 3-$h$4 and at least one health measurement of person 10. Each of tertiary wellness devices 3-1, 3-2, 3-3 and 3-4 further comprise necessary power, computing and communications, all as will be well understood by those skilled in the art. Devices 3-1, 3-2, 3-3 and 3-4 should be considered as exemplary rather than limiting of tertiary devices 3, as many other possible arrangements, configurations, forms, etc., are possible. For example, the related PCT application as well as upcoming FIGS. 4D, 4E and 5B show other secondary 2 and tertiary 3 wellness devices, where again the "primary vs. secondary vs. tertiary" distinction is instructive and non-limiting and where modifications can be made to virtually any primary 1, secondary 2 and tertiary 3 wellness device to cause it to function as another respective classification according to the definitions provided herein.

Referring specifically to FIG. 1D, a significant amount of research and development is producing new types of wearables, either integrated into clothing, shoes, hats, etc., or designed to be fit directly onto the body, ranging from a smartwatch (that fastens, holds around a body part) to a patch (that fastens, sticks to a body part), or even a sensor/device being inserted into the body such as fully or partially under the skin. Some devices are referred to as "biosymbiotic devices" and can be 3D printed based upon 3D scans of the person 10's body, thus providing more comfortable/custom fits supporting longer wear time with commensurate health measurement data collection. Biosymbiotic devices pioneered by engineers at the University of Arizona "can operate continuously using a combination of wireless power transfer and compact energy storage" (see the article "Biosymbiotic Devices: 3D-Printed Personalized, Wireless Wearables That Never Need a Charge" dated Oct. 21, 2021 in the SciTechDaily). The prior related PCT application as well as the present teachings show that any such devices can become tertiary devices 3.

As a careful consideration of the present application and the related PCT application will show, to function as extended-use tertiary devices 3, some wearable device 3's will require sensor means to confirm the state of "clasped," "attached," "affixed," etc., versus the opposite state. As a careful consideration will also show, any wearable device 3 will need to determine a body pattern (b) (such as a heartbeat) for comparison with a like body pattern (b) preferably captured by a companion primary device 1 (see also FIG. 2 for more detail). Furthermore, by adding body ID pattern (a) detection to such a wearable, any of these devices can be further enabled to function as a secondary devices 2, where then further adapting these same now secondary devices 2 into primary devices 1 will be considered as possible but less desirable in comparison to providing means for the secondary devices 2 (or tertiary devices 3) to electronically communicate with primary devices 1, such that primary devices 1 perform the bulk of regiment processing and proof-of-health determination (see especially the related PCT application). Regarding adding body ID pattern (a) detection to such device 3 wearables, the same heartbeat patterns that can function as a confirmation body pattern (b) can be used at some level of measurement as a body ID pattern (a) (as will be understood by those familiar with electrocardiogram (ECG, EKG) biometrics), where a careful consideration will show that heartbeat information is more readily available to most wearables such as "biosymbiotic devices," as opposed to using facial, fingerprint, audio, iris, etc., recognition.

And finally, with respect to FIGS. 1A, 1B, 1C, 1D, 1E and 1F, as well as the upcoming FIGS. 2, 3A, 3B, 3C, 4D, 4E, and 5B, secondary 2 and tertiary 3 wellness devices preferably provide data to a primary wellness device 1-1, 1-2 (or 1-3, see FIG. 3B) that is capable of executing the functions of the intermediary app/"honest broker" as taught in the related applications especially including the PCT application in relation to "proof-of-health" for interacting with an access control system.

Referring next to FIG. 2 the is shown a flowchart of the preferred steps (100 through 114) for authentication of a primary device 1, such as non-wearable mobile device 1-1 or wearable smartwatch 1-2 (or 1-3, see FIG. 3B), followed by the collection of health measurements by the authenticated primary device 1. In step 100, "lockable primary device?", the intermediary app/"honest broker" executing on the primary devices such as 1-1 or 1-2 determines if the primary device 1-1 or 1-2 is "not lockable" (such as smartphone 1-1, which is not a wearable) or "lockable" (such as smartwatch 1-2, which is a wearable), all as first taught in the related PCT application. If the devices is "lockable" (by any of several means discussed in the related PCT application, or as currently known in the art or would be reasonably devised by a person skilled in the art for the purposes stated herein), then the person 10 either knows to or is instructed to lock the device 1 in step 102 "set to locked state" (e.g., by clasping a wearable such as smartwatch 1-2 around their wrist), where once locked the device such as 1-2 is then able to proceed to the step 104 to "determine primary authentication."

As was discussed in the prior and related PCT application, a lockable device such as 1-2 is capable of "taking on-going measurement(s)" (in step 110) up until the time the locked primary device is determined to be "set to (an) unlocked state" (in step 112). Prior to steps 110 and 112, after step 102, a locked primary device such as smartwatch 1-2 is preferably authenticated in step 104 ("determine primary authentication"), which is also the next step for a primary device such as smartphone 1-1 that was determined to be "lockable primary device?"="no" in step 100.

In step 104, the primary device 1 (e.g., but not limited to 1-1, 1-2) uses any of many possible technologies and methods to determine at least one body pattern (a) for (ID), such as but not limited to facial recognition, fingerprint (both depicted), audio/voice recognition, or iris scan (all readily achievable using existing and well-known technology). Many additional body pattern (a) for (ID) technologies exist, such as but not limited to palm prints and heartbeat "signatures" (both readily achievable but not commonly implemented on devices such as 1-1 or 1-2). Regardless of the one or more methods chosen, where for example a smartphone 1-1 preferably determines a combination of body IDs (a) using facial recognition, voice recognition and fingerprint analysis (via sensor 1-1-*s*), and where for example the smartwatch 1-2 determines a body ID (a) via fingerprint analysis (via sensor 1-2-*s*1), the net result is that at least one "current" person 10 biometric (such as the face, finger, iris or voice pattern (a)) is captured for comparison to a "registered" person 10 biometric, all as discussed in the prior related applications. Upon sufficient matching of a current biometric with a prior captured and registered biometric, the person 10 is determined by the honest broker executing on the primary device 1 to be sufficiently authenticated (see prior related applications for a greater understanding).

Still referring to FIG. 2, after step 104, a "not lockable" primary device such as smart phone 1-1 may proceed to "take a concurrent measurement(s)" in step 108 (whereas, as prior discussed, a lockable device such as smartwatch 1-2 may proceed to "take on-going measurement(s)" in step 110). In step 108, as will be appreciated from a careful consideration of the present and prior related teachings, it is beneficial for gaining "public trust" that any one or more health measurements determined by a "not lockable" device such as 1-1, are determined substantially simultaneously (i.e., "concurrently") with the authentication of device 1-1 (in step 104). If this was not the case, it would be possible for a given person 10 to authenticate a "not lockable" device such as smartphone 1-1 (step 104) and then to transfer the device 1-1 to another person (not-10) to determine a health measurement of person not-10 in step 108, thus without this concurrency step 108 is not "publicly trustable" as a method for ensuring that health measurements are being taken "of" person 10.

As a careful consideration of the prior and current teachings will show, it is also desirable that the health measurement(s) taken in step 108 are taken from the body surface being used to confirm the body pattern (a) ID. As a contrary ("not publicly trustable") example, a smartphone 1-1 captures one or more images of person 10 (using its front-facing "selfie" camera) for use in facial recognition (a) during step 104, while concurrently a person (perhaps 10 or not-10) places their finger over the back facing camera, for example to get a measurement of blood-pressure. As a careful consideration will show, the primary device 1-1 authenticating person 10 has no sufficient way to simultaneously confirm that the (health) measurement of blood pressure also relates to person 10. However, if primary device 1-1 or 1-2 is at least using a sensor such as 1-1-*s* or 1-2-*s*1, respectively, the device 1-1 or 1-2 can determine a body pattern for ID (a) off the person 10's fingertip while also determining a health metric (such as blood pressure, pulse, oxygenation levels and even body temperature (see upcoming FIGS. 3A and 3B) concurrently and importantly off the same fingertip of person 10's.

Still referring to FIG. 10 and the concurrent combination of steps 104 and 108, in another arrangement smartphone 1-1 captures a facial image of person 10 for body pattern (a) ID analysis, while also determining a health metric using the same facial image data, where for example a health metric could be the person's current pulse determined using rPPG as discussed both in the prior related PCT application and herein. Two things are important to see. First, for a non-lockable primary device such as a smartphone 1-1, determining a health measurement in step 108 that is "publicly trustable" is preferably done using in part at least the same dataset used for determining the body pattern ID (a). Second, in practice, image analysis is a possible (for example wound analysis) but not typically preferred method for determining health measurements, which is why many wellness devices available in the marketplace do not use cameras and are not based upon image analysis. It is also useful to understand that while some smartphones 1-1 still retain a fingerprint sensor, many such as an iPhone do not, and thus sensor 1-1-*s* would be an adaptation. Furthermore, while fingerprint sensors 1-1-*s* do exist in the marketplace that are capable of also determining at least a person 10's pulse/heartbeat, these sensors where primarily conceived of as a means for combating fingerprint faking, where for example a rubberized finger with a forged print is presented to a traditional fingerprint reader. As a careful consideration will show, by also sensing for a pulse using sensor 1-1-*s* or 1-2-*s*1, it is possible to determine a body ID pattern (a) for authentication of health measurements, to detect a fake fingerprint being presented for example by a rubber finger, to determine a confirmation body pattern (b) for authentication and pairing (see upcoming steps 106-1 through 106-3), and then to possibly further determine at least one health metric (such as blood pressure).

It is noted that the present invention anticipates a new use for sensors such as 1-1-*s* and 1-2-*s*1 that combine fingerprint detection with pulse detection, where the new use is to concurrently determine, from the same "publicly trustable" person 10 body surface, a body pattern ID (a) (i.e., the fingerprint), a body confirmation pattern (b) (i.e., the finger heartbeat 1-*h*2), and zero or more person 10 health measurements. There are other usable alternative fingerprint detection technologies (for example an ultrasonic "3D" fingerprint reader from Qualcomm) developed for determining the fingerprint from a location underneath a portion of the screen area on a device such as 1-1 or 1-2 (sometimes referred to as an "in-screen" fingerprint reader). The present application anticipates using a form of "in-screen" PPM combined with "in-screen" fingerprint detection, such that sensor 1-1-*s* or 1-2-*s*1 could located underneath the respective device 1-1, 1-2's screen.

Still referring to FIG. 2, as a careful consideration of the prior related PCT application and the present teachings will show, using a "lockable" primary device such as wearable smartwatch 1-2 (as opposed to smartphone 1-1), it is possible to determine "publicly trustable" health measurements of the person 10 (step 110) that are not necessarily taken concurrently with the identification/authentication step 104 of person 10. However, as a careful consideration will also show, many useful health measurements available from many existing wellness devices or from anticipated new technologies that will eventually be incorporated into wellness devices, are desirable for authenticating as a part of a publicly-trustable proof-of-health regiment/self-access system, all as first described in the related PCT application. Given this consideration, it is preferable that a not-lockable or lockable primary device 1, such as 1-1 or 1-2 respectively, be able to interface with secondary 2 and tertiary 3 wellness devices for the purpose of further obtaining and authenticating these additional possible health measurements.

In step 106-1, a primary device 1 electronically pairs with a secondary 2 or tertiary 3 wellness device, where communication pairing is well-known in the art. Either prior to or preferably after pairing, "companion" wellness devices 2 or 3 determines and makes known to the primary device 1 if the device 2 or 3 is a "lockable companion device?" in step 200, as well as other pertinent information such as but not including the type of device, types of health measurement(s), as well as the type(s) of confirmation body pattern (b) (such as a heartbeat 2-*h*4 or 3-*h*4) that the device 2 or 3 is capable of determining and providing. If the device 2 or 3 is lockable, for example it is a wearable such as a chest band 2-1, then either automatically or preferably under the request of the primary device 1 the person 10 is directed to lock the device 2 or 3 in step 202, resulting in the determining of an affirmative "set to locked state" being provided by device 2 or 3 to primary device 1 also in step 106-1.

In step 106-2 "determine pair confirmation pattern A," primary device 1 then determines a confirmation (b) body pattern "A", such as a face heartbeat 1-*h*1 using rPPG, or a finger heartbeat 1-*h*2 using PPG embedded in sensor such as 1-1-*s* or 1-2-*s*1. As taught in the prior related PCT application, and as will be understood from a careful consideration of the present teachings, it is also preferable that the confirmation (b) body pattern A, such as 1-*h*1 or 1-*h*2, be taken from a body surface that is concurrently being examined by the primary device for the determining of the body ID pattern (a), such as via facial recognition or fingerprint recognition, respectively. Also preferably concurrent, the paired companion device 2 or 3 in step 206-2 "determine pairing confirmation pattern B" determines and communicates to device 1 a confirmation (b) body pattern "B", such as a finger heartbeat 2-*h*2 or a body heartbeat 2-*h*4 or 3-*h*4, where confirmation (b) body pattern B is of a type that is comparable to confirmation (b) body pattern A being captured by the primary device 1.

In step 106-3 "confirm pairing confirmation A/B match," the primary device 1 compares confirmation (b) body pattern A captured by primary device 1 with confirmation (b) body pattern B captured by the companion device 2 or 3, whereupon sufficient correlation the companion device 2 or 3 is considered by primary device 1 to be "authenticated," and hence any health measurements "taken and communicated" by the companion device 2 or 3, either substantially concurrently in step 208 because the companion devices is "not lockable," or anytime in step 210 for a companion device that is "lockable" and remains locked (thus the measurements of step 210 are taken prior to the determination of being "set to unlocked state" in step 212).

And finally with reference to FIG. 2, as will be appreciated by those skilled in the art of devices and algorithms, the steps presented can be combined with each-other or other new steps, or the steps can be limited (for example excluding the use of not-lockable devices), and some steps can even be omitted, where for example step 108 may not be necessary for some types of primary devices 1. Thus, the flowchart provided in FIG. 2 should be considered as exemplary of a preferred use and embodiment of the present invention, but not as limiting the invention to the specific steps or even the specific order of steps, as other flows will be apparent to those skilled in the necessary arts where these other flows remain within the anticipated scope and spirit of the invention.

Figure 3A:
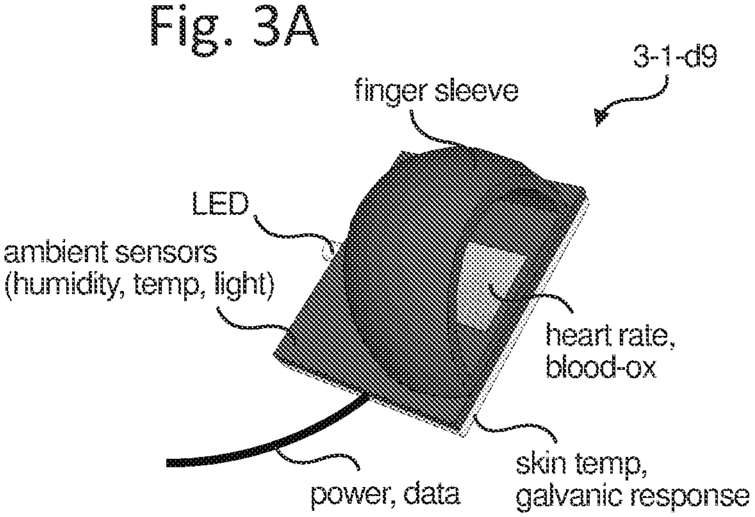
FIG. 3A is a perspective view of a finger-worn touch thermometer 3-1-*d*9 configured as taught in the related PCT application. Touch thermometer 3-1-*d*9 was taught to comprise a contact temperature sensor for determining personal body temperature for example by touching the forehead. The device included a light emitting means such as an LED for use in the line-of-sight authentication process as described in the PCT application. Various ambient sensors were included to determine for example the surrounding humidity, temperature, and light levels, all of which were discussed as potentially impacting the determination of the personal body temperature. The device 3-1-*d*9 also included galvanic response sensors to for example measure the current resistance and capacitance of the skin at the point of contact, also shown to be useful for determining the presence of added substances that might affect the personal body temperature measurement. And finally, device 3-1-*d*9 also included sensors for determining heart rate and blood ox levels, typically accomplished using photoplethysmography (PPG).

Referring next to FIG. 3A, there is shown finger worn device 3-1-*d*9 as first described in the related PCT application. In the PCT application, finger worn device 3-1-*d*9 was taught in multiple configurations, where a preferred configuration included heart rate and blood oxygenation sensor, a skin temperature sensor, skin galvanic (electrical) response sensor(s), ambient sensors for sensing for example humidity, temperature, and light levels as well as a light emitter such as an LED for use in what the PCT application referred to as "light signaling" as a means of device and device measurement authentication. While alternate implementations of the finger worn device can be "wireless" including their own power and computing means, a configuration as described in the PCT application and presently shown used a wired means for receiving power and communication signals from a primary device 1 such as a smartphone and honest broker app 1-1, where the processing of health data captured by the finger worn device 3-1-*d*9 was preferably accomplished on the primary device 1, thus making device 3-1-*d*9 a tertiary device 3 in the terms of categorization being presently taught. Still other variations of finger worn device 3-1-*d*9 were taught in the related PCT application to include a fingerprint body pattern (a) sensor, where this ID-capable variation as prior taught is a secondary device 2 implementation of the finger worn device.

Figure 3B:
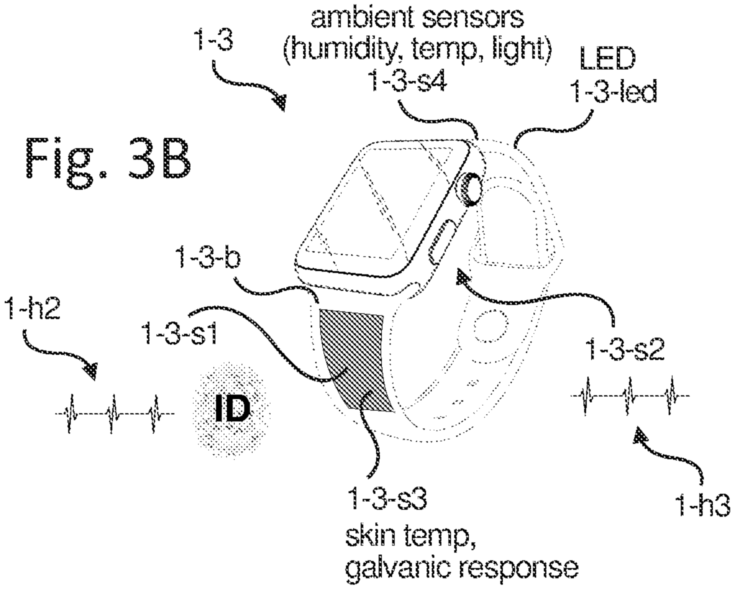
FIG. 3B depicts alternative smartwatch 1-3 that has been further adapted beyond smartwatch 1-2 of FIG. 1A to include sensors found on the touch thermometer 3-1-*d*9 (see FIG. 3A) such that alternative smartwatch 1-3 can then be used to accomplish at least some of the purposes taught with respect to 3-1-*d*9 in the related PCT application (in particular, the reading of personal body temperature off the forehead, see FIG. 3C). The preferred minimum added sensors 1-3-*s*3 include contact sensor(s) for determining skin temperature as well as galvanic response sensors (sometimes referred to as "electrodermal" sensors) for sensing electrical properties of the skin such as resistance and capacitance. Additional preferred added sensors 1-3-*s*4 measure ambient humidity, temperature and light levels. Device 1-3 optionally includes a light emitting means such as an LED 1-3-*led* for use in the line-of-sight authentication process as described in the PCT application.

Referring next to FIG. 3B there is shown alternative smartwatch 1-3 that preferably but not necessarily includes all of the apparatus and teachings of smartwatch 1-2 and has been further adapted to include any one of or any combination of sensors and teachings with respect to finger worn device 3-1-*d*9 (see related PCT application for further discussion), preferably at least including a touch/skin temperature sensor (again, see the related PCT application teaching and purposes) incorporated as sensors 1-3-*s*3, where sensors 1-3-*s*3 are preferably substantially collocated with fingerprint reader/heartbeat sensor 1-3-*s*1 (where sensor 1-3-*s*1 is like sensor 1-2-*s*1 discussed in relation to FIG. 1B).

Figure 3C:
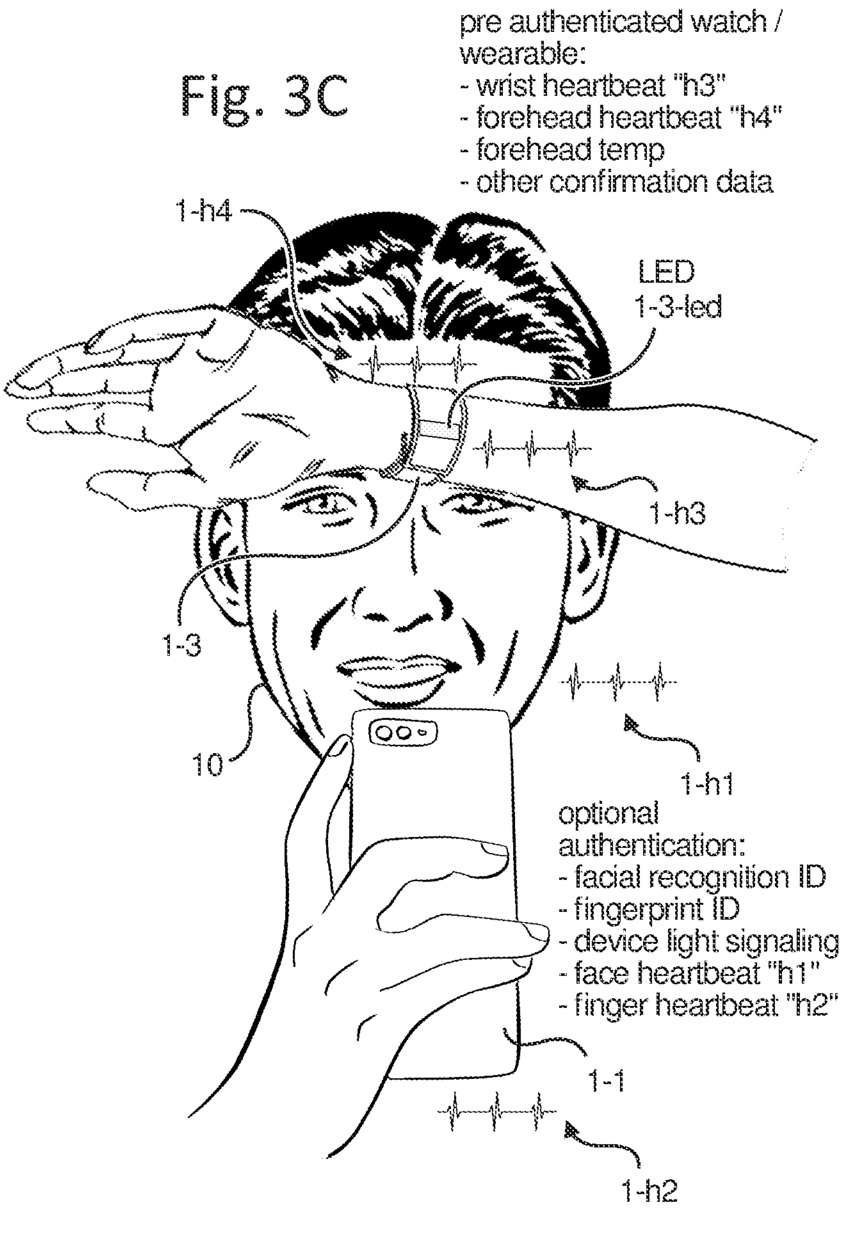
FIG. 3C is a pictorial diagram showing person 10 using alternative smartwatch 1-3 to touch their forehead for taking their personal body temperature while preferably also capturing their forehead-heartbeat 1-*h*4 for authentication comparison to at least their wrist-heartbeat 1-*h*3 as captured by the watch 1-3. Watch 1-3 preferably also captures the skin galvanic responses as well as ambient environment data such as humidity, temperature and light levels. Also depicted, person 10 is optionally using smartphone 1-1 to further authenticate the forehead temperature by determining person 10's facial-heartbeat 1-*h*1 and/or finger-heartbeat 1-*h*2 for comparison with forehead-heartbeat 1-*h*4. If implemented, smartwatch 1-3 uses optional light emitting means 1-3-*led* for conducting line-of-sight authentication with smartphone and app 1-1, all as described in the related PCT application.

By including a touch/skin thermometer 1-3-*s*3, alternative smartwatch 1-3 can then be used to accomplish at least some of the purposes taught with respect to a finger worn device such as 3-1-*d*9 in the related PCT application (in particular, the reading of personal body temperature off the forehead in relation to a public regiment, see also upcoming FIG. 3C). By further including galvanic (electrodermal skin) response sensors (all as taught in the PCT application, especially in relation to a finger worn device such as 3-1-*d*9), additional assurances can be determined with respect to the veracity of the skin temperature measurement, for example by comparing the current electrical condition (resistance, capacitance) of person 10's temperature touch-point (such as the forehead) with a pre-determined baseline. Other preferred added sensors 1-3-*s*4 measure ambient humidity, temperature, and light levels, and as was discussed in the related PCT application, are also useable to ensure the veracity of any given current skin temperature measurement of a person 10. Alternative smartwatch 1-3 preferably also includes wrist sensors 1-3-*s*2 (like sensors 1-2-*s*2 of device 1-2) for determining a wrist heartbeat 1-*h*3, all as prior discussed especially in relation to FIG. 1B.

Modified smartwatch 1-3 optionally includes a light emitting means such as an LED 1-3-*led* for use in the line-of-sight authentication process as described in the PCT application. However, as a careful consideration of the teachings provided herein regarding smartwatch 1-2 (see especially FIG. 1A) will show, since smartwatch 1-2 has been further adapted to include fingerprint reader/heartbeat sensor 1-2-*s*1, smartwatch 1-2 (and therefore also modified smartwatch 1-3, through the use of like fingerprint reader/heartbeat sensor 1-3-*s*1) can "self-authenticate" (thus being a primary device 1), without needing a primary device 1 such as a smartphone 1-1 to accomplish authentication, for example using line-of-sight "light signaling," and as such light emitting means LED 1-3-*led* is useful for additional authentication accuracy, but not mandatory for authentication.

Still referring to FIG. 3B, the marketplace has attempted to put at least ambient temperature sensors into smartphones such as used for a primary device 1-1. Typically, the internal heat generated by the smartphone itself has made these ambient temperature sensors less reliable.

Attempting to add a skin contact/personal temperature sensor (such as depicted in FIGS. 3A and 3B and as discussed in the related PCT application) into a primary device 1-1 implemented with a smartphone is also anticipated to be problematic for at least two reasons: 1) temperature sensing reliability due to the internal heat at times being created by the smartphone, similar to the problems with the ambient temperature sensors, and 2) having an ideal section of surface area on the smartphone to comprise the touch sensor that is both convenient for touch for example to the forehead, and otherwise preferably does not reduce or interfere with the screen/display area, all as will be appreciated by those familiar mobile devices such as smartphones.

However, adding a touch temperature sensor to a wrist wearable primary device 1 such as smartwatch 1-3 does not suffer either of these two disadvantages as will be more apparent from a careful consideration of upcoming FIG. 3C. Touch/skin temperature sensor (along with optional galvanic response sensors) comprising sensors 1-3-*s*3 can be situated on/incorporated "into" the band 1-3-*b* of device 1-3 so as to be sufficiently separated from the electronics (and any corresponding heat buildup) associated with the computing elements of the smartwatch 1-3, while not interfering with the screen/display area and yet still electrically connected to smartwatch 1-3, and while also being conveniently positioned on the band 1-3-*b* so that touching to a body-point of person 10 such as the forehead is easily accomplished.

Regarding the sensing of body temperature, touch sensors currently have at least two key advantages over remote (non-touch) sensors, specifically: 1) by touching the skin the temperature reading will on average be more accurate, and 2) remote sensors typically rely upon IR imagers that are not easily integrated into smartphones (and thus are typically found as standalone devices/"IR temperature guns"). However, new research and development led by Dr. Won Jun Choi of the Center for Opto-Electronic Materials and Devices in the Korea Institute of Science and Technology (KIST) is demonstrating that it is possible to create a thermal-imaging sensor that overcomes the problems (such as heat buildup, device costs) currently restricting the use of thermal imaging sensors in smartphones (such as used in device 1-1).

The present invention anticipates that primary devices 1 will at some future date be able to accomplish the combination of 1) determining body pattern ID (a) for example using facial recognition, 2) determining confirmation body pattern (b) such as a facial heartbeat 1-*h*1 using rPPG, and 3) determining an accurate body temperature for example from the forehead, all using spatially collocated data (i.e., a single image or stream of images) from one or more image sensors, where if multiple sensors the fields-of-view of the sensors are substantially and sufficiently overlapping. As will be understood by those familiar with the necessary arts and smartphone imaging sensors, (1) and (2) above are already available as is (3) to some less reliable extent. Hence (3), determining an accurate body temperature using a smartphone embedded imaging sensor is expected to be better enabled in the future by the new types imaging sensors being developed as prior mentioned. Thus, providing a touch-based spatially collocated sensor capable of determining (1), (2) and (3), such as substantially spatially collocated sensors 1-3-*s*1 and 1-3-*s*3 offers the novel ability to determine a bio-ID (a) (in this case a fingerprint), a bio-pattern (b) (in this case a finger heartbeat) and a bio-health-metric (in this case the finger temperature) over substantially simultaneous same duration of time. Those familiar with the accuracy of sensing body temperatures will recognize that the finger temperature is not as accurate a measure of the core body temperature as the forehead, let alone other even more internal areas of the body (such as the mouth, see FIGS. 5A and 5B).

Referring now to FIG. 3C, this same combination of spatially collocated sensors 1-3-*s*1 and 1-3-*s*3 can be used in a sequential manner to first determine the body ID pattern (a) (a fingerprint) along with body confirmation pattern (b) (the finger heartbeat 1-*h*2) and then to second determine for example a forehead temperature using skin temperature sensor 1-3-*s*3 along with a body confirmation pattern (b) (such as forehead heartbeat 1-*h*4 determined using sensor 1-3-*s*1 or wrist heartbeat 1-*h*3 using sensor 1-3-*s*2), where then first heartbeat 1-*h*2 can be compared to a second heartbeat 1-*h*3 or 1-*h*4 for authentication. As will also be understood from a careful consideration, it is possible to use smartwatch 1-3 to touch a surface that is not the skin of the person 10 that is wearing the watch 1-3, and for this reason it is taught to substantially simultaneously detect a heartbeat (such as forehead heartbeat 1-*h*4) from the same (substantially spatially collocated) skin contact point (such as person 10's forehead), while than also preferably substantially simultaneously detecting a second confirmation heartbeat (such as wrist heartbeat 1-*h*3 using sensors 1-3-*s*2) so that the comparison of contemporaneous heartbeats 1-*h*4 and 1-*h*3 provides the authentication for the measured (e.g., forehead) temperature.

Still referring to FIG. 3C, it is also possible to use alternative smartwatch 1-3 in contemporaneous combination with smartphone 1-1, where smartphone 1-1 with honest broker app is confirming person 10 via facial recognition (thus a body pattern ID (a)) while also determining a confirmation body pattern (b) (i.e., that facial heartbeat 1-*h*1), where then 1-*h*1 is comparable to (forehead) skin heartbeat 1-*h*4 to provide authentication for the measured (e.g., forehead) temperature (see the teachings of the related PCT application for more discussion on "authentication of health measurements"). An advantage of this combination use of 1-1 with 1-3 is that smartwatch 1-3 would then not require a fingerprint reader sensor 1-3-*s*1, although smartwatch 1-3 would still require a pulse sensor for determining 1-*h*4 that is preferably collocated with the skin temperature sensor 1-3-*s*3, where then the careful reader will understand that alternative smartwatch 1-3 is acting as a tertiary device 3, rather than a self-authenticating primary device 1.

In this combination use of 1-1 with 1-3, light emitter 1-3-*led* can also be used to engage with line-of-sight light-signaling between smartphone 1-1 and smartwatch 1-3, thus providing another form of authentication (as compared to body pattern (b) confirmation between 1-*h*1 and 1-*h*4). Thus, the careful reader will see that there are several possible variations of alternative smartwatch 3-1, for use alone or in combination with smartphone 1-1, each variation providing different advantages and tradeoffs, and as such the present application should not be limited to the exemplary depictions (such as the present FIG. 3C). The careful reader will also see that there are several variations of methods for ultimately determining an "authenticated health measurement" that is a skin temperature measurement of person 10 (as depicted). For example, the smartphone device 1-1 could use the finger heartbeat 1-*h*2, in combination or instead of face heartbeat 1-*h*, to be the confirmation body pattern (b) for comparing with either or both of 1-*h*3 or 1-*h*4.

Figure 4A:
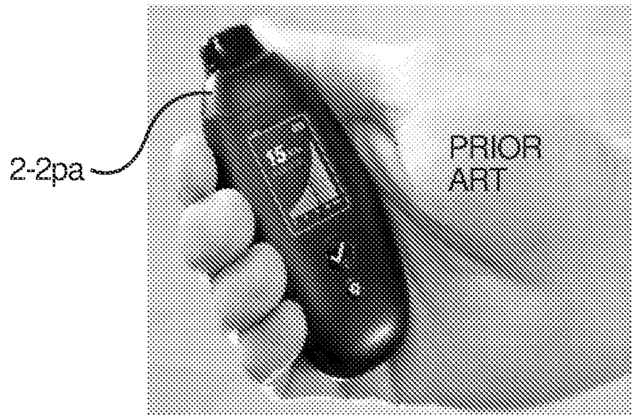
FIG. 4A is an image of a currently available (PRIOR ART) handheld "breath keytone monitor"/breath analyzer 2-2*pa* sold by Biosense as referenced in the related PCT application. In general, there are many types of breath analyzers that are being represented by 2-2*pa*, of which the Biosense is just one example. For example, breath analyzer 2-2*pa* is also meant to represent breath analyzers used to determine the current alcohol level in a person 10, while other examples include detection of current medical conditions, such as but not limited to infectious diseases.

Referring next to FIG. 4A there is shown a PRIOR ART type of a breath analyzer 2-2*pa*, where the breath analyzer is used to detect what are known as "keytones," (all as first discussed in the prior related PCT application). There are many types and purposes for breath analyzers such as 2-2*pa*, for example some analyzers are used to determine blood alcohol levels, and where many new types of important health information are anticipated to be determined from the processing of a person 10's breath as technology and the health marketplaces naturally move forward. What is important to see is that the present teachings especially related to FIG. 4A through FIG. 4E teach a new means for determining "authenticated health measurements" (see related PCT application) from breath analysis of a person 10, regardless of the type of breath analysis.

Figure 4B:
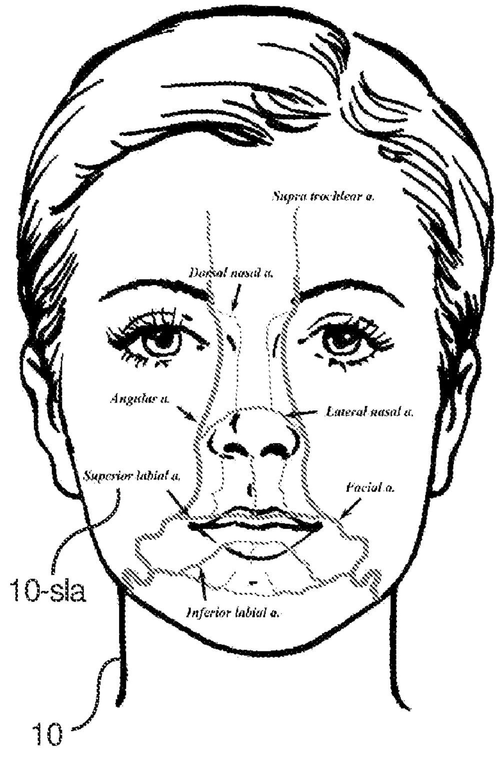
FIG. 4B shows person 10 with an overlay of the human facial arteries. What is important to see is that there are two facial arteries pumping blood through the lips. Namely, the inferior labial artery through the lower lip (not labeled), and the superior labial artery 10-*sla* through the upper lip.

Referring next to FIG. 4B there is shown the face of a person 10 superimposed with a medical graphic of the human facial arteries. Of note are the arteries referred to as the "superior labial artery" 1-*sla* that runs horizontally across the upper lip and the "inferior labial artery" (not labeled) that runs horizontally across the lower lip. Both arteries are considered in the present teachings to be sufficient for supporting the determination of a person 10's lip heartbeat 3-*h*4 (see FIG. 4D) to be used at least as a body confirmation pattern (b), although going forward in the current specification the teachings will focus solely on the upper lip and superior labial artery 1-*sla*.

Figure 4C:
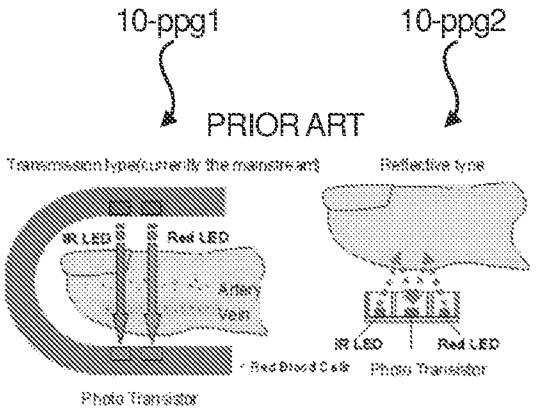
FIG. 4C depicts the well-known apparatus referred to as photoplethysmography (PPG) sensors for detecting blood flow in general and the heartbeat in particular when substantially coming into contact with the skin. PPG sensors include two main arrangements referred to as the "transmission type" and the "reflective type." An example transmission type PPG is a traditional pulse oximeter that clamps over a fingertip. An example reflective type PPG is typically used on the underside of a smartwatch, such as primary device 1-2 (see 1-2-*s*2 in FIG. 1A, bottom view), or an exercise wearable like a "Fitbit."

Referring next to FIG. 4C there is shown well-known (PRIOR ART) photoplethysmography (PPG) apparatus including the "transmission type" 10-*ppg*1 and the "reflection type" 10-*ppg*2. The prior related PCT application discusses PPG sensors in more detail, while there are also significant teachings available in the public domain. For the present application, either type 10-*ppg*1 or 10-*ppg*2 can be implemented to accomplish the goal of determining a person's confirmation body pattern (b) through detection of a pulse/heartbeat preferably from either or both the upper or lower lip areas, but otherwise in the area of the mouth that is consistent with the use of a breath analyzer, although going forward in the current specification the teachings will focus solely on the use of reflective type PPG 10-*ppg*2 used to determine the lip heartbeat 3-*h*4 from the upper lip.

Referring next to FIG. 4D there is shown a perspective view of lip pulse detector 3-5 used for (1) determining a current lip heartbeat 3-*h*4, (2) communicating with a companion health measurement device (such as a breath analyzer 2-2*ba* shown in FIG. 4E or a digital thermometer 2-3*dt* shown in FIG. 5B), and (3) communicating with a primary device 1 such as a smartphone 1-1 or smart watch 1-2, 1-3. Lip pulse detector 3-5 preferably comprises a mouthpiece 3-5-*mp* comprising a PPG lip pulse sensor 3-5-*s*1, where mouthpiece 3-5-*mp* is constructed to include coupling means 3-5-*c* for physically coupling with the companion health device (such as breath analyzer 2-2*ba* or digital thermometer 2-3*dt*), where many shapes, forms and materials used for mouthpiece 3-5-*mp* are possible and many shapes, forms and materials used for coupling means are possible, such that the present teachings should not be unnecessarily limited based upon the current depictions of FIG. 4D.

In the present depiction, lip pulse sensor 3-5-*s*1 for (1) determining the current lip heartbeat 3-*h*4 is shown as situated on a vertically aligned portion of the mouthpiece 3-5-*mp* that is expected to come into contact with the upper lip of person 10 during use. As will be understood by those familiar with PPG sensors and the human mouth, many possible arrangements for either preferred PPG sensor 10-*ppg*2 (reflective type) or sensor 10-*ppg*1 (transmission type) are possible, and therefore the present invention should not be unnecessarily limited to the present exemplary depiction. What is important to see is the lip pulse detector 3-5 includes means for and is constructed to enable the capturing of a current confirmation body pattern (b), such as the lip heartbeat 3-*h*4.

In the present depiction, coupling means 3-5-*c* are portrayed as a cavity within mouthpiece 3-5-*mp* through which the companion device (such as 2-2*ba* or 2-3*dt*) may be inserted and withdrawn (i.e., in some fashion engaged, coupled, aligned or otherwise properly situated for accomplishing the intentions described herein, where many variations are possible), where electronic physical-contact means (not depicted) are preferably provided within the cavity for supporting communication (2) between the lip pulse detector 3-5 and the companion device, such as 2-2*ba* or 2-3*dt*. Many such electronic physical-contact means are known in the art, where it is also possible to use electronic non-contact means, for example where detector 3-5 communicates wirelessly with the companion device such as 2-2*ba* or 2-3*dt*, and therefore the present invention should not be unnecessarily limited to the present exemplary depiction and preferred description.

It is even possible that no direct means for communication (2) between the lip pulse detector 3-5 and a companion device (such as 2-2*ba* or 2-3*dt*) are provided, where for example both detector 3-5 and any companion device instead individually communicate (3) with a primary device 1, where then the primary device 1 relays any information or signaling between device 3-5 and a companion (such as 2-2*ba* or 2-3*dt*) that would be necessary, all as will be well understood by those familiar with electronic devices and communication and control between electronic devices. What is important to see is that lip pulse detector 3-5 can minimally determine and provide a current confirmation body pattern (b) such as lip heartbeat 3-*h*4 for use by any one of or any combination of a companion health device such as 2-2*ba* or 2-3*dt* or a primary device such as 1-1, 1-2 or 1-3.

What is also important to understand is that while the current teachings provide for a modular design that separates lip pulse detection into a single physical unit 3-5 for coordination with other possible distinct devices for making health measurements such as breath analysis (device 2-2*ba*) or oral temperature (device 2-3*dt*), it is also possible to create a single integrated unit that for example analyzes the breath of person 10 while also determining a current heartbeat such as lip pulse 3-*h*4 (preferably from the outside or inside mouth region), when then further also preferably, but not necessarily or at least not necessarily in real-time, communicating with a primary wellness device 1, as many arrangements are possible without departing from the true spirit and teachings provided herein.

Referring next to FIG. 4E, there is depicted lip pulse detector 3-5 being used in combination with a companion breath analyzer 2-2*ba*, where analyzer 2-2*ba* is preferably physically and electronically coupled with detector 3-5 so as to function in coordination, in some sense as a single integrated unit which is an alternate possible construction as previously mentioned. Person 10 preferably inserts the breath input opening of analyzer 2-2*ba* into the cavity 3-5-*c* of detector 3-5, after which devices 3-5 and 2-2*ba* are in communication, either directly and/or indirectly via a primary wellness device such as 1-1, 1-2 or 1-3. The purpose of this depicted arrangement, and any of many possible alternatives, is to provide means for determining an authenticated health measurement based at least in part upon samples of the person 10's current breath, for which many possible health measurements are already known and will become known, all of which are considered to fall within the scope of the present invention.

As a careful reading of the present invention as well as the related PCT application will show, there are many ways of providing authentication ensuring that any of health measurements sampled, sensed, or otherwise determined by an oral cavity examination device such as breath analyzer 2-2*ba* are "of" a person 10. An oral examination device such as 2-2*ba* senses and determines one or more breath detectable characteristics of person 10, where other variations of an oral examination device might alternatively or in combination process a saliva sample or body temperature to determine at least one health measurement. Any of authenticated health measurement(s) determined and authenticated by the combination of at least lip pulse detector 3-5 and breath analyzer 2-2*ba*, in any of many possible configurations including as an single device, with or without the concurrent interaction of a primary device 1, can then be associated with the health data and any zero or more health regiments being processed by the intermediary ("honest broker") app executing on a primary wellness device 1 such as 1-1, 1-2 or 1-3 (see FIG. 2).

As depicted, in one configuration breath analyzer 2-2*ba* is further adapted with a fingerprint/heartbeat sensor 2-2-*s*1 (like sensors 1-1-*s*, 1-2-*s*1, 2-1-*s*1 and 1-3-*s*1) such that person 10 is preferably identified by a body ID pattern (a) (fingerprint) while substantially simultaneously at least one health measurement is determined based at least in part upon breath from person 10 being input by the analyzer 2-2*ba*, while also substantially simultaneously a first (A) confirmation body pattern (b) (finger heartbeat 2-*h*2) is determined by the analyzer 2-2*ba* while a second (B) confirmation body pattern (b) (lip heartbeat 3-*h*4) is determined by the analyzer lip pulse detector 3-5, whereupon sufficient correlation of patterns (A) and (B), the substantially concurrent health measurement(s) of analyzer 2-2*ba* are deemed as authenticated to be "of" person 10.

Still referring to FIG. 4E, a careful consideration will show many possible ways for assuring that any health measurement determined by analyzer 2-2*ba* based upon currently input breath is authenticatable to be "of" a person 10, especially in consideration of the cooperation between devices 3-5, 2-2*ba* and a primary wellness device 1. Therefore, the present depiction and associated teachings should not be considered as unnecessarily limiting, but rather as exemplary. For example, it is possible that analyzer 2-2*ba* (portrayed as a self-authenticating secondary device 2) omits fingerprint/heartbeat sensor 2-2-*s*1, where the determined current coupling between analyzer 2-2*ba* provides assurance the that current lip heartbeat (3-*h*4) (B) determined by companion lip pulse detector 3-5 is combinable for authentication with health data determined by analyzer 2-2*ba*, where then this authentication is provided by a primary device 1 that is concurrently confirming both a body ID pattern (a) and a first (A) confirmation body pattern (b), where a sufficient correlation between patterns (A) and (B) allows for authentication. Again, there are many possible arrangements all within the anticipated scope and spirit of the present invention, including that the combination of two separate devices 3-5 and 2-2*ba* are implemented as a single integrated unit.

Figure 5A:
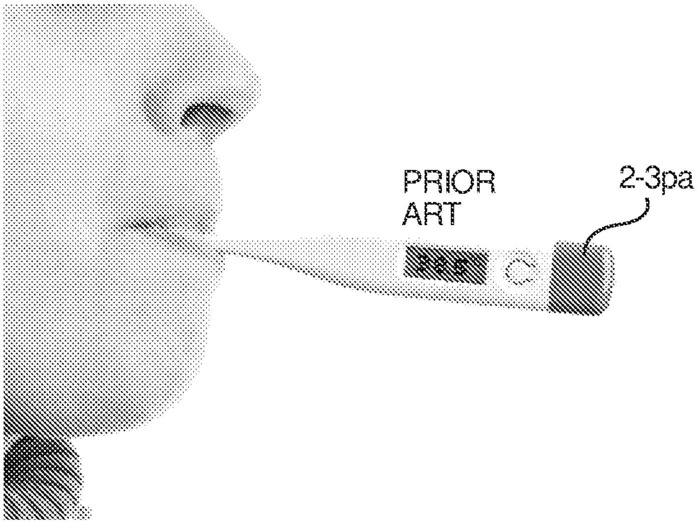
FIG. 5A is an image of a currently available (PRIOR ART) digital thermometer 2-3*pa* for which there are many manufacturers.
Figure 5B:
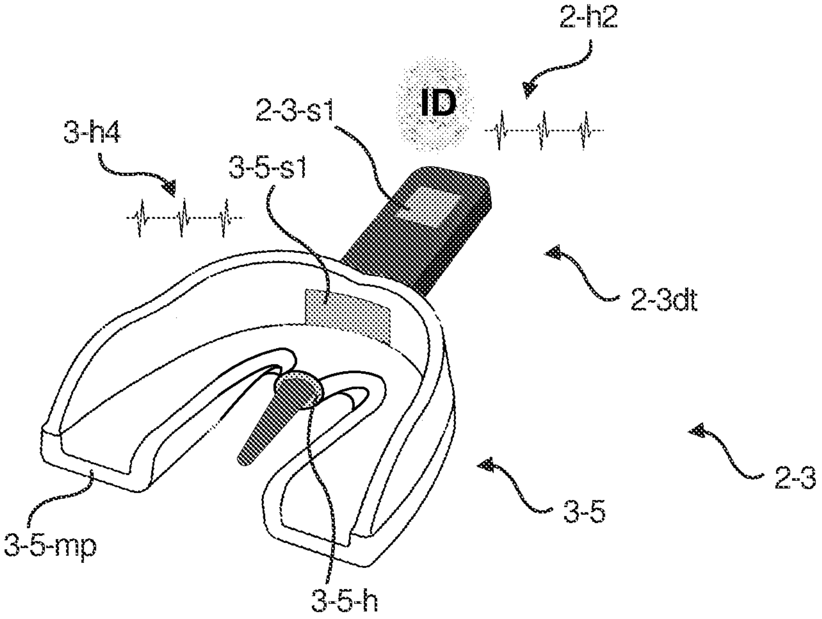
FIG. 5B, like FIG. 4E, shows the physical and functional combination of a further adapted digital thermometer 2-3*dt* with lip pulse detector 3-5, where the combination forms authenticating oral thermometer 2-3. Like breath analyzer 2-2*ba*, digital thermometer 2-3*dt* preferably comprises a combination fingerprint reader/heartbeat sensor 2-3-*s*1 for determining finger-heartbeat 2-*h*2 as well as apparatus for physically coupling and electronically engaging and/or otherwise communicating with lip pulse sensor 3-5 such that sensor 3-5 determines the time and duration of engagement, preferably used at least in part to trigger lip pulse 3-*h*4 measurement via the PPG sensor(s) 3-5-*s*1. Digital thermometer 2-3*dt* may also comprise electronic components for communicating with any of a primary wellness device such as smartphone and app 1-1 or smartwatch 1-2, 1-3. There are many possible arrangements and configurations of authenticating oral thermometer 2-3, where some combinations comprise a multi-part configuration including physically separable lip pulse unit 3-5 and digital thermometer unit 2-3*dt*, whereas other configurations (not depicted) form a single integrated device 2-3 with the necessary combination of apparatus and methods comprising 3-5 and 2-3*dt*.

Referring next to FIG. 5A there is shown a PRIOR ART type of oral digital thermometer 2-3*pa*, where the oral thermometer 2-3*pa* is used to detect a current body temperature (all as first discussed in the prior related PCT application). The oral device 2-3*pa* should not be limited to determining a body temperature, where device 2-3*pa* being inserted into the mouth can also contact the skin and at least the bodily fluid of saliva, and where this other skin contact, or saliva contact/input, can at least in part be useful for determining a health measurement. What is important to see is that the present teachings especially related to FIG. 4A, 4B, 4C, 4D, 4E, 5A and FIG. 5B teach new means for determining "authenticated health measurements" (see related PCT application) from an oral sampling of a person 10.

Referring next to FIG. 5B there is depicted the combination of the lip pulse detector 3-5 being used in combination with a companion oral digital thermometer 2-3*dt*, where thermometer 2-3*dt* is preferably physically and electronically coupled with detector 3-5 to function in coordination, in some sense as a single integrated unit which is an alternate possible construction as previously mentioned. Person 10 preferably inserts the oral temperature sensing "distal" end of thermometer 2-3*dt* into the cavity 3-5-*c* of detector 3-5, after which devices 3-5 and 2-3*dt* are in communication, either directly and/or indirectly via a primary wellness device such as 1-1, 1-2 or 1-3. The purpose of this depicted arrangement, and any of many possible alternatives, is to provide means for determining an authenticated health measurement based at least in part upon samples of the person 10's oral cavity, for which many possible health measurements are already known and will become known, all of which are considered to fall within the scope of the present invention.

As a careful reading of the present invention as well as the related PCT application will show, there are many ways of providing authentication ensuring that any of health measurements sampled, sensed, or otherwise determined by an oral cavity examination device such as thermometer 2-3*dt* are "of" a person 10. An oral examination device such as 2-3*dt* senses and determines the body temperature of person 10, where other variations of an oral examination device might alternatively or in combination process a saliva sample to determine at least one health measurement. Any of authenticated health measurement(s) determined and authenticated by the combination of at least lip pulse detector 3-5 and thermometer 2-3*dt*, in any of many possible configurations including as a single device, with or without the concurrent interaction of a primary device 1, can then be associated with the health data and any zero or more health regiments being processed by the intermediary ("honest broker") app executing on a primary wellness device 1 such as 1-1, 1-2 or 1-3.

As depicted, in one configuration thermometer 2-3*dt* is further adapted with a fingerprint/heartbeat sensor 2-3-*s*1 (like sensors 1-1-*s*, 1-2-*s*1, 2-1-*s*1, 1-3-*s*1 and 2-2-*s*1) such that person 10 is preferably identified by a body pattern (a) (fingerprint) while substantially simultaneously at least one health measurement is determined based at least in part upon the oral cavity temperature being sensed the thermometer 2-3*dt*, while also substantially simultaneously a first (A) confirmation body pattern (b) (finger heartbeat 2-*h*2) is determined by the thermometer 2-3*dt* while a second (B) confirmation body pattern (b) (lip heartbeat 3-*h*4) is determined by the analyzer lip pulse detector 3-5, whereupon sufficient correlation of patterns (A) and (B), the substantially concurrent health measurement(s) of thermometer 2-3*dt* are deemed as authenticated to be "of" person 10.

Still referring to FIG. 5B, a careful consideration will show many possible ways for assuring that any health measurement determined by thermometer 2-3*dt* based upon currently sensed oral temperature is authenticatable to be "of" a person 10, especially in consideration of the cooperation between devices 3-5, 2-3*dt* and a primary wellness device 1. Therefore, the present depiction and associated teachings should not be considered as unnecessarily limiting, but rather as exemplary. For example, it is possible that thermometer 2-3*dt* (portrayed as a self-authenticating secondary device 2) omits fingerprint/heartbeat sensor 2-3-*s*1, where the determined current coupling between thermometer 2-3*dt* provides assurance the that current lip heartbeat (3-*h*4) (B) determined by companion lip pulse detector 3-5 is combinable for authentication with health data determined by thermometer 2-3*dt*, where then this authentication is provided by a primary device 1 that is concurrently confirming both a body ID pattern (a) and a first (A) confirmation body pattern (b), where a sufficient correlation between patterns (A) and (B) allows for authentication. Again, there are many possible arrangements all within the anticipated scope and spirit of the invention, including that the combination of two separate devices 3-5 and 2-3*dt* are implemented as a single integrated unit.

CONCLUSION AND RAMIFICATIONS

A careful understanding of the present teachings considering the prior two related applications will show that a traditional wearable such as a smartwatch, "activity tracker," or similar can be further adapted to operate as a primary wellness device capable of both self-authentication and of paring with and authenticating any other primary, secondary, or tertiary wellness device. This novel ability greatly increases the amount of authenticated health measurements available to the primary device for use in monitoring a person according to one or more public health regiments or protocols.

There are known devices in the marketplace, such as manufactured by Nymi, that are wearables capturing at least a body ID pattern (a) that is a fingerprint, and a body ID pattern (a) that is a heartbeat signature. Nymi recognizes the fingerprint to be more accurate for identification of a person than the heartbeat signature and uses the conjunction of IDs to increase the veracity of initial personal authentication. A constraint of the Nymi solution is that a person must register with a system outside of their personal control, often referred to as a "centralized system," where registering implies providing personal information for association with at least one biometric, or data derived from at least one biometric, for example a "mathematical template" derived from a fingerprint. The centralized-solutions then allow a person streamlined access through a controlled gateway, where streamlined implies a minimal effort with minimal time to ideally become "fully transparent" to the person, and hence for example the person simply taps an NFC reader with their wearable to unlock a door, authenticate a lab result or open a secure document on their computer. The Nymi solution implements a necessarily non-anonymous method of communication with the physical or virtual access gateway to the premises or document, respectively, where the gateway is associated with a system that maintains information about the person that is confirmed by the wearable.

In the prior related and present teachings, the person's identifying information is not revealed to the access gateway but rather the gateway is assured by communication with the primary device that the person that is attempting to gain access has an authenticate honest broker app on their primary device, where the honest broker app is verifiable to the gateway but otherwise not associated with the person. The honest broker in this sense is acting like as an escort that is both known to and trusted by the premises and known to and trusted by the person, even though the premises and the person are not "known" to each other. It is up to the premises to recognize and trust the honest broker, and the honest broker to recognize and trust the person.

In the prior related applications, the honest broker requires the person to registration one or more personal biometrics that can at any time be used to authenticate the person via correlation with current biometric(s), and in this sense the person becomes recognized by the honest broker.

The related PCT application as well as the present teachings add to this "person recognition" the concept of recognizing that a current health measurement is being made "of the recognized person," hence "authenticated health measurements." These authenticated health measurements are then used to derive an authenticated current health status for the recognized person. At some point, when a person desires access to a premises or gathering, all that is necessary is that they identify themselves to the honest broker (using one or more current biometrics) in a manor trustable to the premises, for example (but not limited to) when standing within a premises geofence (see the prior related applications). Once re-identified within for example a premises geofence, the honest broker assures the premises gateway (access control system) that the person the honest broker recognizes has followed and currently complies with a health protocol ("regiment") recognized by the premises, and hence the health status of the person (whose identity remains unknown to the premises) is "vouched for" by the honest broker.

The present and prior related applications teach the novel use of body ID patterns (a) (e.g., face, finger, voice, iris) and confirmation patterns (b) (e.g., heartbeat) for the authentication of health measurements determined by companion devices, where the diversity of the types of measurements made available by various companion devices (e.g., wearables, patches, smart scales, exercise equipment, breath analyzers, and body fluid analyzers) greatly increases the veracity of the authenticated health status derived by the primary device from the authenticated health measurements "of" the person.

While the present application is taught with respect to a heartbeat determined by a companion wellness device and used as a confirmation body pattern (b), where the confirmation process compares two substantially concurrent heartbeats (b) captured by two electronically paired devices, it is possible that for example that the companion wellness device captures one or more health measurements while concurrently determining as related data the person's current heartbeat/ECG/EKG signature as a body ID pattern (a). Hence, the companion device can work "off-line" to collect health measurements, ensuring that each health measurement determined by the companion device is associated with a substantially concurrently determined heartbeat signature (a). Each health measurement(s) is thus paired with a heartbeat (a) signature, the data of which can then be transmitted at a later time to the primary device for authentication.

In this arrangement, it is also possible that the companion device as a wearable omits sensors for determining a "locked" or "attached to body" state confirmation. Each time the companion wellness device collects a health measurement being naturally "of" a body, what is minimally needed is that the wellness device concurrently determines a body ID pattern (a) (such as a heartbeat signature) using the same "proximal body" "of" the person. This functionality is accomplished for example if the sensed data used at least in part to determine the health measurement is also repurposed at least in part for determining the body ID pattern (a).

Examples are skin contact sensors that determine body measurements while also detecting the ECG/EKG heartbeat signature (a), or a camera that uses image analysis to measure a wound while also detecting a heartbeat signature (a). Given a wearable with multiple sensors (such as a smartwatch or chest band), it is also possible that one set of sensors is responsible for determining the body ID pattern (a) (such as the heartbeat signature), while at the same time other distinct sensors, not necessarily collocated with respect to the person's body but otherwise assured to be measuring the person's body, concurrently capture other health measurements. In this case each distinct health measurement, from multiple possibly non collocated sensors, is validated by a substantially concurrent measurement of a body ID pattern (a) such as the heartbeat signature.

To increase veracity, each non-collocated sensor on the same wellness device can also determine a confirmation body pattern (b) (e.g., the person's current heartbeat), such that the same wellness device uses a first ID sensor that is capturing the body ID pattern (a) (heart ECG/EKG signature) to also determines a pattern (b) (current heartbeat) for authenticating each non-collocated (non-ID) sensor on the same wellness device, where after authenticating the sensed data from each non-ID sensor using pattern (b), the same wellness device can store and later transmit all pattern (b) verified health measurements (from any authenticated non-collocated non-ID sensor) to a companion primary device along with a pattern (a) captured concurrently by the same wellness device's ID sensor.

For example, a chest band wearable, with no locking sensors, is affixed to a person and uses multiple sensors spaced throughout the chest band to sense data about the person every 15 minutes. Each separately spaced/non-collocated sensor (x) determines a current confirmation heartbeat pattern (b)-(x) at the time of measurement (m)-(x), where at least one sensor is an ID-sensor capable of also determining a body ID pattern (a) (such as the heartbeat ECG/EKG signature). A computing element on the chest band or in communication with the chest band aggregates each measurement (m)-(x) with its current pattern (b)-(x) along with one associated pattern (a)-(b) also concurrently captured by the wellness device, where the computing element verifies that each measurement with confirmation pattern (m)-(b)-(x) correlates with the concurrent ID and confirmation (a)-(b) and stores the multiple measurements as (m)-(a), preferably with a time stamp, for later use and sharing with another primary wellness device.

A careful understanding of the present invention will show a system for use in private that is able to determine and otherwise collect multiple on-going health measurements from a multiplicity of connected wellness devices, where this large and varied set of authenticated health data forms a valuable on-going assessment of a person's current health state. This data can for example be used to establish important norms, such as body temperatures at different times of the day, or a person's resting heart rate. Using these norms, it is possible to implement what is referred to in the art as "pre-symptomatic" detection of an infection disease, such as COVID-19 (see "Pre-symptomatic detection of COVID-19 from smartwatch data," published Nov. 18, 2020, in the journal of Nature Biomedical Engineering, authored by Mishra, et al.). Pre-symptomatic detection of an infectious disease is greatly advantaged by capturing multiple on-going systems, often from multiple/disparate devices, all of which is made "publicly trustable" by the teaching of the prior applications and new teachings provided herein.

The present invention and prior related applications discuss many uses of tracking an authenticated health status, where some uses are for controlling/governing access to a premises or gathering, but other uses are for tracking a verifiable health status of a person, where verifiability is useful for at least insurance and law enforcement purposes. The present invention is also anticipated to have value to the person for tracking their on-going multi-symptom state, which for example can help with disease tracking (see "The wearable device that could help to detect cancer" published Oct. 8, 2021, in Nature).

Those familiar with wellness devices will recognize that significant effort is being expended to create new and better sensors and especially wearable sensors (see "Graphene made with lasers for wearable health devices" published Sep. 3, 2021, on Phys.org). Most of these current and future anticipated devices will be in contact with the skin or under the skin of a person and as such are expected to be able to readily determine a current heartbeat confirmation body pattern (b), and as such with each new advancement in sensor and wearable technology, the present and prior teachings provide an extensible general platform for tracking a personal and publicly trustable health state, where for example a person's smartwatch as a primary wellness device serves as an authenticated health data aggregator and also communicates with their smartphone primary wellness device for providing an alternate user interface and additional authentication methods.

Those familiar with the current state of smartwatches will recognize that there is a wide range in features and cost, where very low-cost devices such as provided by Xiaomi do not include full "watch-like" functionality as compared to an Apple watch, and where "activity trackers" such as the Fitbit offer some form of visual user interface but more minimal watch functionality. As a careful consideration will show, any of these various implementations of wrist wearables, as well as other types of wearables, can all be further adapted as taught in the present and related applications to implement any of primary, secondary, or tertiary wellness devices. As will also be well understood by those familiar with smartwatches, it is also possible to include a camera in the smartwatch to at least perform facial recognition functions as taught herein with respect to the smartphone implementation of a primary device.

The prior PCT application also taught a new form of contact tracing that extended the dataset determined using current contract tracing techniques to include as contact relevant data the current health status of any two or more person's deemed to be coming into contact. These PCT teachings remain applicable with the new primary wellness device teachings provided herein, including the prior PCT teachings for contact tracing and social distance tracking with respect to a novel "active mask" technology. Hence, the present invention's primary devices, both wearable and non-wearable, are anticipated to perform contact tracking with other wearable or non-wearable primary devices as well as the prior taught "active mask" technology.

We claim:

1. A method for using a combination of a wearable device and one or more health measurement devices for determining and authenticating the provenance of a multiplicity of health measurements to be of a same pre-registered person, where the multiplicity is determined over a continuous duration of time for which the wearable device is confirmed to be affixed to the same pre-registered person, where the identity of the person is confirmed to match a pre-registered biometric ID only once and prior to taking any of the multiplicity of health measurements during the continuous duration, and where each of the wearable device and the health measurement device comprises a heartbeat sensor, comprising the steps of:

affixing the wearable device the body of the person such that the wearable heartbeat sensor is held in an operative sensing position respective of the body of the person for detecting a temporal heartbeat pattern of the person, where the wearable determines secured state information confirming and indicative of a current state of being affixed that begins the continuous period, where the continuous period is ended at such a subsequent time that the secured state information is indicative of the wearable device no longer being affixed to the body of the person;

at a time concurrent or subsequent to the beginning of the continuous period, using an authenticating device or otherwise ID sensor to concurrently determine a biometric ID comprising either of a facial image or a fingerprint of the person collocated with a first temporal heart beat pattern of the person, using the wearable heartbeat sensor to concurrently determine a second temporal heart beat pattern of the person, and (i) comparing the biometric ID to a prior known biometric of a pre-registered person, (ii) comparing the first and second concurrent temporal heart beat patterns, and (iii) authenticating that the person to whom the wearable is currently securely affixed is the pre-registered person upon the successful comparisons of (i) and (ii), and at a time subsequent to authentication and still within the continuous period, establishing communications with a health measurement device, using the wearable device to determine a new second temporal heart beat pattern different from the authentication second temporal heart beat pattern, concurrently using the health measurement device to concurrently determine one or more health measurements along with a third temporal heart beat pattern of a currently measured person, receiving the one or more health measurements and the third temporal heart beat pattern from the health measurement device, (iv) comparing the new second temporal wearable heart beat pattern and third concurrent temporal health device heart beat patterns, (v) authenticating that the currently measured person of whom the health measurement device is currently sensing is the same person as the pre-registered person upon the successful comparison (iv), and aggregating the received one or more health measurements as authenticated measurements respective of the same pre-registered person.

2. The method of claim 1 wherein the third temporal heartbeat is determined in colocation with the one or more health measurements such that determination is made from the same or an adjacent surface point on the body of the person prohibiting the measurement of two separate persons.

3. The method of claim 1 further comprising the steps of:

determining the third temporal heartbeat from the mouth area of the person when using a breath analyzer;

determining the third temporal heartbeat from a foot of the person when using a smart scale;

determining the third temporal heartbeat from a hand of the person when engaging with exercise equipment;

determining the third temporal heartbeat from the torso of the person when engaging with a chest band;

determining the third temporal heartbeat from the body point to which a patch is affixed to the person when engaging with a body patch;

determining the third temporal heartbeat from the fingertip of the person when engaging with a finger worn device, and determining the third temporal heartbeat from the mouth area of the person when using a digital oral thermometer.

4. The method of claim 1 further adapted for determining and maintaining an on-going current health status of the person, further comprising the steps of:

at a time prior to the continuous period, using the authenticating device to receive one or more public regiments comprising one or more rules for determining and maintaining the on-going current health status of the person, and processing at least two health measurements separately determined and authenticated at different times based at least in part upon the one or more public regiments to determine and maintain the on-going current health status of the person.

5. The method of claim 4 further adapted for assuring the public of the authenticated current health status of the person before granting the person access to a premises or otherwise gathering of people, further comprising the steps of:

providing an access control system for engaging with the person prior to granting access by the person to the premises or otherwise gathering of people, where the person uses either of the wearable device or the authenticating device to provide the on-going current health status of the person to the access control system during the engagement, and using the access control system to grant or deny access by the person to the premises or otherwise gathering of people based at least in part upon the received current health status of the person.

6. The method of claim 1, wherein authentication of the wearable or health measurement device either additionally or alternatively to either of (ii) or (iv) comprises optical challenge-response signaling in which a control signal causes emission of a temporal light pattern that is validated to authenticate device association.

7. The method of claim 1 wherein the step (ii) for comparing the first and second concurrent temporal heart beat patterns is alternatively replaced by step (ii-alt) concurrent temporal light signaling, where the authenticating device comprises or is further adapted to comprise a camera, where the wearable device comprises or is further adapted to comprise a light emitter, further comprising the steps of:

during authentication of the person to whom the wearable device is currently affixed, using the authenticating device camera to capture a multiplicity of images comprising both a view of the face of the person and the wearable device;

concurrently with the capturing of the multiplicity of images:

determining and communicating a control signal to the wearable device;

causing the wearable device to emit a response signal for imaging by the camera, where the response signal is based at least in part upon the control signal;

analyzing the multiplicity of images to determine a facial image of the person for use as the biometric ID of the person in the comparison (i);

analyzing the multiplicity of images to determine the response signal for use in (ii-alt) comparison of the control signal with the response signal, and (iii-alt) authenticating that the person to whom the wearable is currently securely affixed is the pre-registered person upon the successful comparisons of (i) and (ii-alt).

8. The system of claim 1 wherein either of the wearable device, a band for affixing the wearable to the body of the person, or a separate external device is or otherwise comprises the authenticating device or otherwise ID sensor.

9. A health assessment system comprising a wearable device and one or more health measurement devices for determining on-going health information authenticated to be relating to a same pre-registered person, comprising:

(a) the wearable device comprising:

a wearable heartbeat sensor for determining a wearable heartbeat of the person, where the wearable heartbeat sensor is oriented to be in operative sensing contact with a wearable location on the body of the person, and where the wearable device is affixed to the body of person such that the wearable heartbeat sensor remains in operative and detectable contact with the wearable location during the on-going receiving and authenticating of the health information;

either of an ID sensor or communication means for exchanging data with an ID sensor, where the ID sensor concurrently determines from an ID location of the body of the person that is different from the wearable location both of a current biometric ID of the person and an ID sensor temporal heartbeat pattern of the person;

an optional wearable secured sensor for determining wearable currently secured to person data;

either of a first computing element or communication means for communicating with a first computing element, where the first computing element at an initial time concurrently (i) compares the current biometric ID with a pre-registered ID of a person, (ii) receives and compares the ID temporal heartbeat pattern with the concurrent wearable temporal heartbeat pattern, and (iii) at least in part uses either of the concurrent wearable temporal heartbeat pattern or the wearable currently secured data to determine if the wearable is currently affixed to the body of the person, and where upon successful determination of (i), (ii), and (iii) the first computing element associates any future wearable temporal heartbeat pattern determined by the wearable heartbeat sensor to be associated with the pre-registered ID during the on-going time commencing at the initial time up until such a subsequent time when the determination (iii) indicates that the wearable device is no longer in operative contact with the body of the person;

(b) the one or more health measurement devices, where each of the one or more health devices comprises:

a health sensor for determining any of the on-going health information;

either of the health sensor or a distinct health device heartbeat sensor for determining concurrent with the on-going health information a device temporal heartbeat pattern of a person currently engaging with the each health device;

communication means for providing the on-going health information and the concurrent device temporal heartbeat pattern to the wearable device or otherwise the first computing element, and (c) where either of the first computing element or otherwise a second wearable computing element at an on-going time subsequent to the initial time concurrently (iv) receives and compares a concurrent wearable temporal heartbeat pattern with the concurrent device temporal heartbeat pattern, and where upon successful comparison of (iv) the first or second computing element (v) associates the concurrently provided on-going health information with the pre-registered ID such that the on-going health information is authenticated to be of the same pre-registered person.

10. The system of claim 9 wherein the current biometric ID is any of a facial image, a fingerprint, or a heartbeat signature any of which are used for comparison with a pre-known and pre-registered biometric ID, wherein the comparison (iv) of the concurrent wearable temporal heartbeat pattern with the concurrent device temporal heartbeat pattern is performed without reference to stored biometric templates, pre-registered heartbeat characteristics, pre-known bio-information, or a biometric ID, such that the comparison establishes physiological correspondence between devices rather than biometric identification of the person.

11. The system of claim 9 wherein the wearable secured sensor is any of a electro-mechanical sensor for sensing the open and closed state of a band being used to clasp the wearable to the person, or an electronic sensor such as a heartbeat sensor for determining a temporal heartbeat pattern, and wherein the secured to person data is at least representative of or otherwise interpretable as indicating the states of open or closed, affixed/attached to body or not affixed/not attached to body.

12. The system of claim 9 wherein the ID sensor is either a camera or a fingertip sensor, where the camera is used to capture a multiplicity of images comprising a view of the face of the person to concurrently determine both the facial image for use as the current biometric ID and the ID sensor temporal heartbeat pattern, where the fingertip sensor is used to sense a surface of a fingertip of the person to concurrently determine both the fingerprint for use as the current biometric ID and the ID sensor temporal heartbeat pattern.

13. The system of claim 12 wherein either of the wearable device, a band for affixing the wearable device to the body of the person, or a separate external device comprises both the ID sensor and the first computing element.

14. The system of claim 9 wherein the one or more health measurement devices for determining any of the on-going health information comprise any one of:

a breath analyzer for measuring the breath, saliva, oral temperature, or other oral characteristics of the person, where the breath analyzer further comprises the device heartbeat sensor for determining the temporal heartbeat pattern from either the face, the lip, or the mouth of the person;

a smart scale for measuring the body weight and other body characteristics of the person, where the smart scale comprises the device heartbeat sensor for determining the temporal heartbeat pattern from the foot of the person;

an exercise equipment for measuring the energy expenditure or other body characteristics of the person, where the exercise equipment comprises the device heartbeat sensor for determining the temporal heartbeat pattern from the hand or otherwise body of the person;

a chest band for measuring the circulatory, respiratory, or other body characteristics of the person, where the chest band comprises the device heartbeat sensor for determining the temporal heartbeat pattern from the torso of the person;

a body patch for measuring bio-metrics of the person, where the body patch comprises the device heartbeat sensor for determining the temporal heartbeat pattern from a body-contact-point where the patch is affixed;

a finger-tip sensor for measuring the characteristics regarding the blood, or skin of the person, where the finger-tip sensor comprises the device heartbeat sensor for determining the temporal heartbeat pattern from the fingertip of the person, and a digital thermometer for measuring the temperature or orally accessible characteristics of the person, where the digital thermometer comprises the device heartbeat sensor for determining the temporal heartbeat pattern from the internal oral cavity of the person.

15. The system of claim 9 wherein the first computing element further determines and updates a current assessment of a health status of the person, where the current assessment is determined based at least in part upon the use of one or more regiments conforming to a public protocol and specifying one or more rules and based at least in part upon two or more health datum comprising the on-going health information, where the two or more health datum are each determined at different times within the on-going time and each correspond to different device temporal heartbeat patterns taken on either of the same each health device or on different each health devices and are thus authenticated using different wearable temporal heartbeat patterns taken at different times.

16. The system of claim 15 further comprising an access control system operated or otherwise used to limit access to either of a premises or otherwise gathering of people, where prior to entering the premises or gathering the person provides requisite data respective of the current health status of the person to the access control system, and where the access control system either allows or denies access to the premises or gathering based at least in part upon the current health status of the person.

17. The system of claim 16 where the first computing element is a component of a mobile device in communications with the wearable device, where the first computing element or otherwise the mobile device obtains the one or more regiments and during the on-going time receives the two or more datum from either of the wearable device or the one or more health devices, and where the first computing element or otherwise the mobile device determines and updates the current assessment of the health status of the person and provides the sufficient requisite data respective of the current assessment of the health status of the person to the access control system.

18. The system of claim 9, wherein authentication of the wearable or health measurement device either additionally or alternatively to either of comparisons (ii) or (iv) comprises optical challenge-response signaling in which a control signal causes emission of a temporal light pattern that is validated to authenticate device association.

19. The system of claim 9 where both the ID sensor and the first computing element are components of a mobile device in communications with the wearable device, where the ID sensor is a camera used for capturing a multiplicity of images comprising both a view of the face of the person and the wearable device, where the mobile device provides a control signal to the wearable device, where the wearable device either comprises or is further adapted to comprise a light emitting component and causes the light emitting component to emit a response signal based at least in part upon the control signal, and where either additionally or alternatively to the determination and use of the concurrent wearable temporal heartbeat pattern and the ID temporal heartbeat pattern for performing comparison (ii) the mobile device analyzes the multiplicity of images to both determine a facial image of the person for use as the current biometric ID for comparison (i) and to determine the response signal of the wearable device for a comparison (ii-alt) with the control signal, and where upon the successful comparison (ii-alt) either additionally or alternatively to (ii) the first computing device associates any future wearable temporal heartbeat pattern determined by the wearable heartbeat sensor to be associated with the pre-registered ID during the on-going time commencing at the initial time up until such a subsequent time when the determination (iii) indicates that the wearable device is no longer in operative contact with the body of the person.

20. The system of claim 9 wherein the device temporal heartbeat is determined in colocation with the any of the on-going health information such that determination is made from the same or an adjacent surface point on the body of the person prohibiting the measurement of two separate persons.

* * * * *